United States Patent [19]

Beck et al.

[11] Patent Number: 4,914,127

[45] Date of Patent: Apr. 3, 1990

[54] 3-DEMETHYLMEVALONIC ACID DERIVATIVES, A PROCESS FOR THEIR PREPARATION PHARMACEUTICAL PRODUCTS BASED ON THESE COMPOUNDS, THEIR USE AND INTERMEDIATES

[75] Inventors: Gerhard Beck; Bela Kerekjarto, both of Frankfurt am Main; Hans-Hermann Lau, Bad Soden am Taunus; Günther Wess, Erlensee, all of Fed. Rep. of Germany

[73] Assignee: Hoechst Aktiengesellschaft, Frankfurt am Main, Fed. Rep. of Germany

[21] Appl. No.: 320,924

[22] Filed: Mar. 8, 1989

Related U.S. Application Data

[63] Continuation of Ser. No. 900,887, Aug. 27, 1986, abandoned.

[30] Foreign Application Priority Data

Aug. 29, 1985 [DE] Fed. Rep. of Germany ....... 3530797
May 7, 1986 [DE] Fed. Rep. of Germany ....... 3615446

[51] Int. Cl.$^4$ .................. A61K 31/365; C07D 309/30
[52] U.S. Cl. ....................... 514/460; 549/60; 549/292; 549/472; 549/417; 546/268; 560/53
[58] Field of Search ................. 549/60, 292, 417, 472; 546/268; 560/53; 514/460

[56] References Cited

U.S. PATENT DOCUMENTS 4,440,927 4/1984 Prugh ................................ 549/292
4,588,715 5/1986 Damon, II ........................ 549/292
4,622,338 11/1986 Baran et al. ...................... 549/292
4,710,513 12/1987 Willard et al. ................... 549/292

FOREIGN PATENT DOCUMENTS 0680038 5/1983 European Pat. Off. ............ 549/292
0164049 12/1985 European Pat. Off. ..

OTHER PUBLICATIONS

Stokker et al., "3-Hydroxy-3-methylglutaryl-etc", J. Med. Chem., (1986), 29, 170-181.
Chemical Abstract No. 99: 38364d, 1983.

Primary Examiner—Richard L. Raymond
Assistant Examiner—Ba K. Trinh
Attorney, Agent, or Firm—Finnegan, Henderson, Farabow, Garrett & Dunner

[57] ABSTRACT

3-Demethylmevalonic acid derivatives of the formula I (δ-lactone) and Ia (corresponding dihydroxycarboxylic acid derivative)

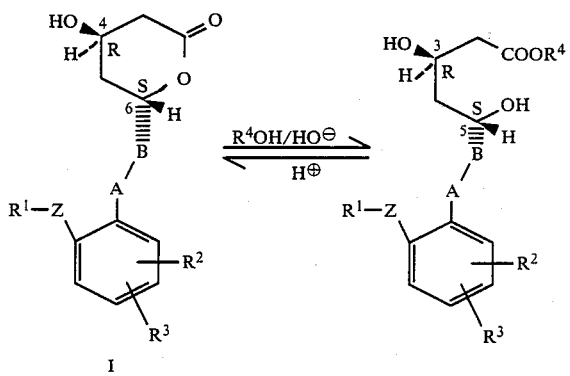

in which A-B, Z, $R^1$, $R^2$, $R^3$ and $R^4$ have the indicated meanings, a process for the preparation of these compounds, their use as medicaments and pharmaceutical products are described. In addition, new intermediates for the preparation of the compounds of the formula I and Ia are described.

5 Claims, No Drawings

3-DEMETHYLMEVALONIC ACID DERIVATIVES, A PROCESS FOR THEIR PREPARATION PHARMACEUTICAL PRODUCTS BASED ON THESE COMPOUNDS, THEIR USE AND INTERMEDIATES

This application is a continuation of application Ser. No. 06/900,887, filed Aug. 27, 1986, now abandoned.

Derivatives of 3-hydroxy-3-methylglutaric acid (HMG) and of mevalonic acid have been described as inhibitors of cholesterol biosynthesis (M. T. Boots et al., J. Pharm. Sci. 69, 306 (1980), F. M. Singer et al., Proc. Soc. Exper. Biol. Med. 102, 370 (1959), H. Feres, Tetrahedron Lett. 24, 3769 (1983)). 3-Hydroxy-3-methylglutaric acid itself exhibits a significant cholesterol-lowering action in the rat and in human trials (Z. Beg, Experimentia 23, 380 (1967), ibid 24, 15 (1968), P. J. Lupien et al., Lancet 1978, 1, 283).

Endo et al. (Febs. Letter 72, 323 (1976), J. Biol. Chem. 253, 1121 (1978)) reported on the inhibition of 3-hydroxy-3-methylglutaryl-coenzyme-A reductase (HMG-CoA reductase), the rate-determining enzyme of cholesterol biosynthesis, by the fermentation product "Compactin". Brown et al. (J. Chem. Soc. 1165 (1976)) determined the chemical structure and the absolute configuration of "Compactin" by a combination of chemical, spectroscopic and radiocrystallographic methods and were able to show that "Compactin" is a derivative of 3-demethylmevalonic acid lactone.

Compactin derivatives which inhibit the activity of HMG-CoA reductase have already been described (G. E. Stokker et al., J. Med. Chem. 28, 347–358 (1985)).

The present invention relates to new synthetic analogs of "Compactin" of the general formula I

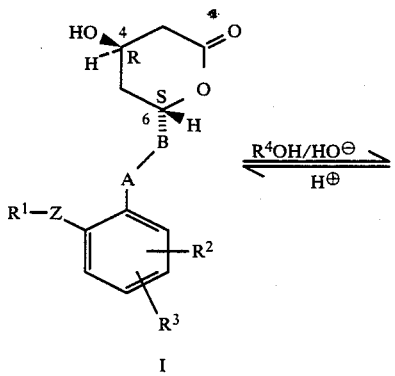

I in the form of the δ-lactone depicted in the formula I or in the form of the dihydroxy acid derivative Ia. In the formulae:

A-B denotes a radical of the formula —CH=CH— or —CH$_2$—CH$_2$—,

Z denotes a —CH$_2$— or —CH$_2$—CH$_2$— group,

R$^1$ denotes a cycloaliphatic hydrocarbon radical which has 3 to 7 carbon atoms and is optionally substituted with 1 or 2 methyl groups, denotes a phenyl radical which can be substituted in the nucleus 1–3 times by halogen, trifluoromethyl, alkyl or alkoxy, each having 1–6 carbon atoms, or by hydroxymethyl, or denotes a furyl, thienyl or pyridyl radical, it being possible for the heteroaromatic radicals to be substituted 1–2 times by halogen, trifluoromethyl, alkyl or alkoxy, each having 1–6 carbon atoms, R$^2$ and R$^3$ denote hydrogen, halogen, trifluoromethyl, alkyl or alkoxy, each having 1–6 carbon atoms, R$^4$ denotes hydrogen or a straight-chain or branched C$_1$–C$_5$-alkyl radical, benzyl, benzyl which is substituted 1–2 times by C$_1$–C$_4$-alkyl or denotes halogen, alkali metal or ammonium (NH4$^\oplus$) or ammonium ion which is substituted with C$_1$–C$_4$-alkyl or hydroxy-C$_1$–C$_4$-alkyl.

The invention relates to the pure enantiomers having the absolute configuration 4R,6S which is indicated in the general formula I, the open-chain carboxylic acids and esters and salts having the absolute configuration 3R,5S.

Among the substituents R$^1$, the following are preferred:

Cyclopentyl, cyclohexyl, or a phenyl radical which can be substituted in the nucleus 1–3 times by halogen, trifluoromethyl, hydroxymethyl, or alkyl or alkoxy having 1 to 4 carbon atoms, a furyl, thienyl or pyridyl radical, it being possible for the heteroaromatic radicals to be substituted 1–2 times by halogen, trifluoromethyl, or alkyl or alkoxy having 1 to 4 carbon atoms.

Among the substituents R$^2$ and R$^3$, the following are preferred:

Hydrogen, halogen, trifluoromethyl, alkyl or alkoxy, each having 1 to 4 carbon atoms.

Among the substituents R$^4$, the following are preferred:

Hydrogen, methyl, ethyl, isopropyl, isobutyl, benzyl, sodium, potassium, ammonium, and trishydroxymethylmethylamine.

Among the substituents R$^1$, those which are listed below are particularly preferred:

Cyclopentyl, cyclohexyl or an unsubstituted phenyl radical or phenyl which is substituted by halogen, trifluoromethyl, hydroxymethyl, C$_1$–C$_4$-alkyl or C$_1$–C$_4$-alkoxy, or a furyl, thienyl or pyridyl radical, it being possible for the heteroaromatic radicals to be substituted once by halogen, trifluoromethyl, C$_1$–C$_4$-alkyl or C$_1$–C$_4$-alkoxy, in particular the radicals:

Cyclopentyl, cyclohexyl, phenyl, 4-chlorophenyl, 2-chlorophenyl, 3-chlorophenyl, 4-bromophenyl, 4-fluorophenyl, 4-methylphenyl, 4-fluoro-3-methylphenyl, 3-trifluoromethylphenyl, 4-trifluoromethylphenyl, 4-methoxyphenyl, 3-methoxyphenyl, 3-methylphenyl, 3,4,5-trimethoxyphenyl, 3-furyl, 2-furyl, 2-thienyl, 3-thienyl, 3-pyridyl, 4-pyridyl, 2,6-dimethyl-4-pyridyl, 3-hydroxymethylphenyl, 3-ethylphenyl, 3-isopropylphenyl, 3-isobutylphenyl, 3-ter.-butylphenyl and 2-chloro-3-thienyl.

Among the substituents R$^2$ and R$^3$, the following are particularly preferred:

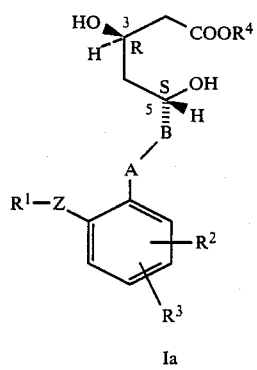

Ia

Hydrogen, 2-methyl, 2-trifluoromethyl, 2,4-dimethyl, 2-methyl-4-chloro, 2-chloro-4-methyl, 2,4-bistrifluoromethyl, 2-ethyl, 2-isopropyl, 2-isobutyl, 2-chloro-, 2-fluoro-, 2-bromo, 2,4-dichloro, 2,4-difluoro, 2-methoxy, 4-methoxy and 2,4-dimethoxy.

Among the substituents $R^4$, the following are particularly preferred:

Hydrogen, methyl, ethyl, benzyl, sodium, potassium, amonium and trishydroxymethylmethylamine.

The invention furthermore relates to a process for the preparation of compounds of the formulaie I and Ia, which comprises:

(a) reaction of the phosphonium salts of the formula II

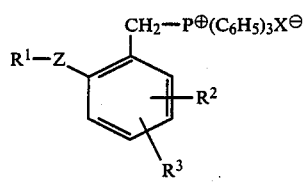

in which $R^1$, $R^2$, $R^3$ and Z have the meaning indicated for formula I, and X is Cl, Br or I, with the chiral aldehyde of the formula III

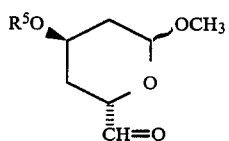

in which $R^5$ denotes a protective group which is stable to bases and weak acids, for example the

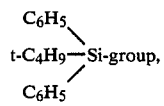

to give a compound of the formula IV

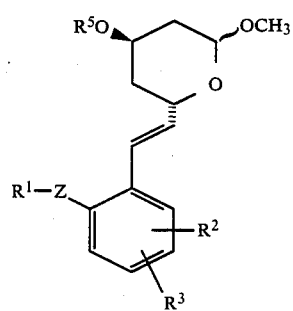

in which $R^1$, $R^2$, $R^3$ and Z have the meaning given for formula I, $R^5$ has the meaning given for formula III (and A-B represents the (—CH=CH—) group), (b) acid hydrolysis of the methyl acetal group in a compound of the general formula IV to give a lactol of the formula V

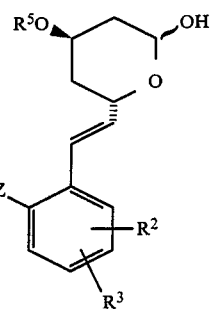

in which $R^1$, $R^2$, $R^3$ and Z have the meaning given for formula I, $R^5$ has the meaning given for formula III (and A-B represents the (—CH=CH—) group, (c) oxidation of the compound of the general formula V to give a lactone of the formula VI

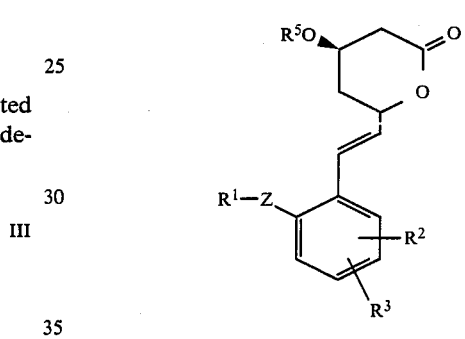

in which $R^1$, $R^2$ and $R^3$ and Z have the meaning given for formula I, $R^5$ has the meaning given for formula III (and A-B represents the (—CH=CH—) group), (d) elimination of the protective group $R^5$ in a compound of the general formula VI to give a compound of the formula I in which $R^1$, $R^2$, $R^3$ and Z have the meanings indicated for formula I, and A-B represents the (—CH=CH—) group, where appropriate hydrogenation of a compound of the general formula I in which A-B represents a (—CH=CH—) group to give a compound of the general formula I in which A-B represents a (—CH$_2$—CH$_2$—) group, it also being possible to carry out the hydrogenation on the compounds of the formulae IV, V or VI to give corresponding compounds in which A-B represents the (—CH$_2$—CH$_2$—) group, where appropriate conversion of a hydroxy lactone I into the corresponding free hydroxy acids Ia or their salts, or, where appropriate, preparation of the correspondng esters from the free hydroxy acids Ia or from the hydroxy lactone I.

The phosphonium salts of the general formula II which are used as starting materials in the process according to the invention are obtained, when Z=CH$_2$ and $R^1$, $R^2$ and $R^3$ have the meaning given for general formula I, by, for example, reaction of the corresponding substituted benzyl halides of the general formula XIII (cf. scheme 1)

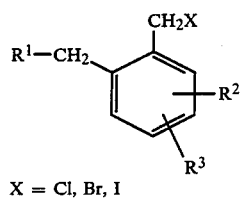

X = Cl, Br, I with triphenylphosphine in acetonitrile, toluene or other comparable solvents (cf. Examples 7a–i). For the preparation of the substituted benzyl halides XIII, it is possible, when $R^1$, $R^2$ and $R^3$ have the meaning indicated for the general formula I, to employ a process analogous to that described by L. A. Walter et al., J. Heterocycl. Chem. 14, 47 (1977) (scheme 1-route A). Depending on $R^1$ (cf., for example, Table 1) it is advantageous to follow synthetic route B (cf. also Examples 1, 4, 5 and 6) for the preparation of the compound of the general formula XIII (scheme 1).

Scheme 2

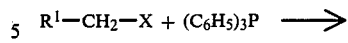

XIV

X = Br, Cl

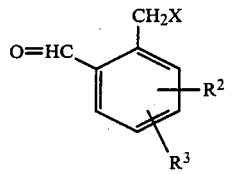

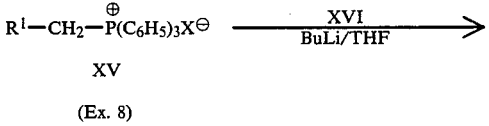

XV (Ex. 8)

Scheme 1

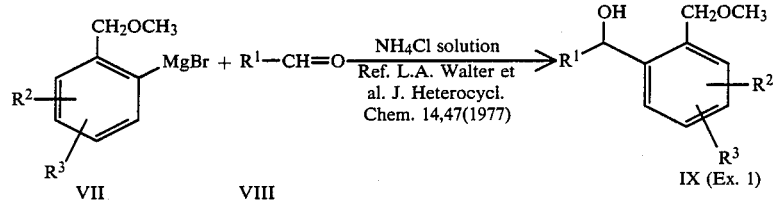

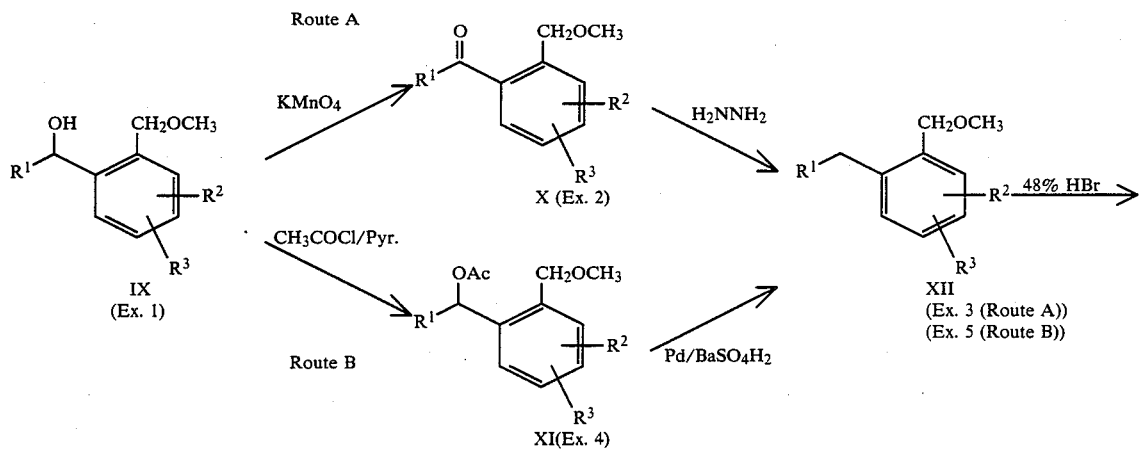

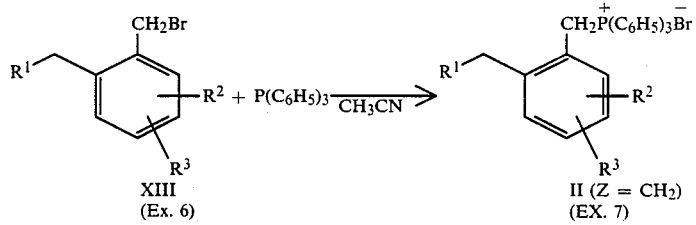

The phosphonium salts of the genral formula II which are used as starting material in the process according to the invention are obtained, when Z is $CH_2$—$CH_2$ and $R^1$, $R^2$ and $R^3$ have the meaning mentioned for general formula I, as depicted in scheme 2 (cf. also Examples 8 to 11).

-continued
Scheme 2

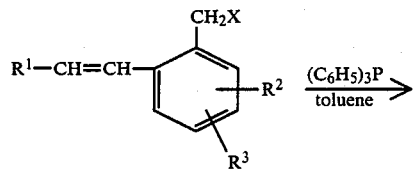

XVII (Ex. 9)

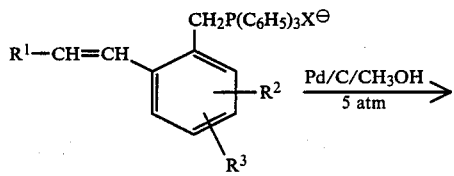

XVIII (Ex. 10)

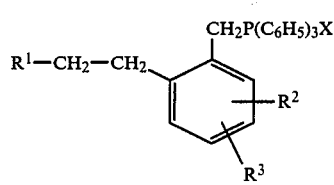

II (Ex. 11)

(Z = —CH$_2$—CH$_2$—)

The chiral aldehyde of the formula III which is used as starting material in the process according to the invention is obtained by a process known from the literature (Yuh Lin, J. R. Falck, Tetrahedron Letters 23, 4305–4308 (1982)) from the corresponding alcohol by oxidation with, for example, CrO$_3$.

The reaction of the chiral aldehyde of the formula III with a phosphonium salt of the formula II by the Wittig method (for example Wittig, Haag, Chem. Ber. 88, 1654 (1955)) results in the compounds of the formula IV, a preferred embodiment comprising dissolution or suspension of the phosphonium salts of the formula II in a solvent such as tetrahydrofuran, dimethyl sulfoxide or DME, and liberation of the corresponding phosphoranes with a suitable strong base such as, for example, sodium hydride, potassium tert.-butylate, Li ethylate or butyllithium, and then addition of the aldehyde of the formula III and allowing reaction to take place at −10° C. to +50° C. for 1–6 hours.

This results in the compounds of the formula IV mainly in the form of a mixture of the E/Z olefins. Mixtures of E/Z olefins can, whereappropriate, be separated by chromatography. The pure Z olefins can also be obtained as described by G. Drefahl, Chem. Ber. 94, 907 (1961), by irradiation of the E/Z mixture in solutions such as, for example, toluene or nitrobenzene.

The corresponding pure E olefins can be obtained as described by De Tar et al. in J. Amer. Chem. Soc. 78, 474 (1955) by heating the E/Z mixtures in solution in the presence of iodine.

The methyl acetal protective group in the compounds of the formula IV can be selectively eliminated in the generally customary manner by acid hydrolysis, preferably using a mixture of glacial acetic acid, tetrahydrofuran and water in the ratio 3:2:2 at +20° to +90° C. in 6–24 hours.

The oxidation of the compounds of the formula V to give a lactone of the formula VI can be carried out by oxidizing agents such as CrO$_3$x2Pyr, or pyridinium chlorochromate in inert solvents such as, for example, methylene chloride or chloroform. Another possibility for the oxidation comprises reaction with thioanisole/Cl$_2$/NEt$_3$ in carbon tetrachloride, or reaction with DMSO/oxalyl chloride/NEt$_3$ at −20° C.

For the preparation of the compounds of the formula I the protective group R$^5$ in the compounds of the formula VI is eliminated. This can take place with strong acids, such as 5-normal hydrochloric acid or sulfuric acid at −10° to +30° C., or with fluoride ions, preferably by dissolving the compounds of the formula VI in tetrahydrofuran or diethyl ether and adding a mixtue of tetrabutylammonium fluoride and glacial aceticacid followed by stirring at 0° C. to 40° C. for between 1 and 12 hours.

Compounds of the formula I in which A-B represents a (CH=CH) group are hydrogenated by a generally customary method, advantageously at temperatures between 20° and 40°, with hydrogen in the presence of a metal catalyst, preferably palladium, platinum, PtO$_2$ or PdO$_2$, to give compounds of the formula I in which A-B denotes a —CH$_2$—CH$_2$— group. This hydrogenation can be carried out under atmospheric pressure in customary solvents such as tetrahydrofuran, ethyl acetate, methanol, lower molecular weight alcohols, glacial acetic acid or chloroform, or in autoclaves under elevated pressure at 2–50 atmospheres. The hydrogenation of the —CH=CH— group can also be carried out on compounds of the formulae IV, V or VI.

The resulting compounds of the formula I can be isolated in a straightforward manner by evaporating off the solvent, where appropriate after chromatographic purification.

The compounds of the formula I are obtained in optically pure form. With regard to the configuration of the double bond (A-B)=—CH=CH—, E/Z mixtures are obtained, and these can be separated by chromatography, or isomerized to the E form, at all stages of the synthesis (cf. in this context De Tar et al. J. Amer. Chem. Soc. 78, 475 (1955)).

Compounds of the formula I in the form of the δ-lactone can be hydrolyzed in an alkaline medium to give the corresponding salts of the dihydroxy acids, for example using NaOH or kOH in a low molecular weight alcohol such as methanol, or in ethers such as dimethoxyethane or THF, where appropriate in the presence of water. The alkali metal cation in the resulting salts of the dihydroxy acids can be replaced by any desired cations after acidification in ion exchangers in the customary manner. For this, for example, the dihydroxy acids are allowed to run through a column packed with a cation exchanger such as, for example, one based on polystyrene/divinylbenzene (®Amberlite CG-150 or ®Dowex-CCR-2). The cation exchanger is loaded with the desired cation, for example with ammonium ions derived from a primary, secondary or tertiary amine. The desired salt is obtained by evaporating the eluate.

Ammonium salts of the dihydroxy acids, which are derived from a primary, secondary or tertiary amine, can also be prepared by addition of an equimolar amount of the appropriate amine to the free dihydroxy acids in an alcoholic solution, and evaporation of the solvent.

The free dihydroxy acids Ia of the δ-lactones I can be esterified by customary methods, for exmple using a diazoalkane. Thus, for example, compounds of the for- If the aldehyde of the formula III is not in the form of the pure enantiomer it is also possible for mixtures of the anantiomeric final products to be produced, which can be separated by generally customary processes.

Apart from the compounds described in the Examples, the following compounds can be prepared by the process according to the invention:

| | |
|---|---|
| (+)-E-6S-[2-(2-(2-(4-Fluorophenyl)ethyl)-6-chlorophenyl-ethenyl]- | 4R-hydroxy-3,4,5,6-tetrahydro-2H-pyran-2-one |
| (+)-E-6S-[2-(2-(2-(3-Trifluoromethylphenyl) ethyl)-6-chlorophenyl-ethenyl]- | 4R-hydroxy-3,4,5,6-tetrahydro-2H-pyran-2-one |
| (+)-E-6S-[2-(2-(2-(3-Methoxyphenyl)ethyl)-6-chlorophenyl-ethenyl]- | 4R-hydroxy-3,4,5,6-tetrahydro-2H-pyran-2-one |
| (+)-E-6S-[2-(2-(2-(4-Chlorophenyl)ethyl-6-Horophenyl-ethenyl]- | 4R-hydroxy-3,4,5,6-tetrahydro-2H-pyran-2-one |
| (+)-E-6S-[2-(2-(2-(Cyclohexyl)ethyl)-6-chlorophenyl-ethenyl]- | 4R-hydroxy-3,4,5,6-tetrahydro-2H-pyran-2-one |
| (+)-E-6S-[2-(2-(2-(2-Methylphenyl)ethyl)-6-methylphenyl-ethenyl]- | 4R-hydroxy-3,4,5,6-tetrahydro-2H-pyran-2-one |
| (+)-E-6S-[2-(2-(2-(4-Fluorophenyl)ethyl)-4,6-dimethylphenyl-ethenyl]- | 4R-hydroxy-3,4,5,6-tetrahydro-2H-pyran-2-one |
| (+)-E-6S-[2-(2-(2-(4-Fluorophenyl)ethyl)-4,6-dichlorophenyl-ethenyl]- | 4R-hydroxy-3,4,5,6-tetrahydro-2H-pyran-2-one |
| (+)-E-6S-[2-(2-(2-(4-Fluorophenyl)ethyl)-4,6-difluorophenyl-ethenyl]- | 4R-hydroxy-3,4,5,6-tetrahydro-2H-pyran-2-one |
| (+)-E-6S-[2-(2-(2-(4-Fluorobenzyl)-6-chlorophenyl-ethenyl]- | 4R-hydroxy-3,4,5,6-tetrahydro-2H-pyran-2-one |
| (+)-E-6S-[2-(2-(2-(4-Fluorobenzyl)-6-fluorophenyl-ethenyl]- | 4R-hydroxy-3,4,5,6-tetrahydro-2H-pyran-2-one |
| (+)-E-6S-[2-(2-(2-(Chlorobenzyl)-6-chlorophenyl-ethenyl]- | 4R-hydroxy-3,4,5,6-tetrahydro-2H-pyran-2-one |
| (+)-E-6S-[2-(2-(2-(2-Methylbenzyl)-6-methylphenyl-ethenyl]- | 4R-hydroxy-3,4,5,6-tetrahydro-2H-pyran-2-one |
| (+)-E-6S-[2-(2-(2-(Cyclohexylmethyl)-6-chlorophenyl-ethenyl]- | 4R-hydroxy-3,4,5,6-tetrahydro-2H-pyran-2-one |
| (+)-E-6S-[2-(2-(2-(4-Fluorobenzyl)-4,6-dimethylphenyl-ethenyl]- | 4R-hydroxy-3,4,5,6-tetrahydro-2H-pyran-2-one |
| (+)-E-6S-[2-(2-(2-(4-Chlorobenzyl)-4,6-difluorophenyl-ethenyl]- | 4R-hydroxy-3,4,5,6-tetrahydro-2H-pyran-2-one |
| (+)-E-6S-[2-(2-(2-(4-Fluorobenzyl)-4,6-dichlorophenyl-ethenyl]9 - | 4R-hydroxy-3,4,5,6-tetrahydro-2H-pyran-2-one |
| (+)-E-6S-[2-(2-(2-(4-Fluorophenyl)ethyl)-4,6-difluorophenyl-ethyl]- | 4R-hydroxy-3,4,5,6-tetrahydro-2H-pryan-2-one |
| (+)-E-6S-[2-(2-(2-(Cyclohexylmethyl)-6-chlorophenyl-ethyl]- | 4R-hydroxy-3,4,5,6-tetrahydro-2H-pyran-2-one |
| (+)-E-6S-[2-(2-(2-(Cyclohexylmethyl)-4,6-dimethylphenyl-ethenyl]- | 4R-hydroxy-3,4,5,6-tetrahydro-2H-pyran-2-one |
| (+)-E-6S-[2-(2-(2-(Cyclohexylmethyl)-4-methyl-6-chloro-phenyl-ethenyl]- | 4R-hydroxy-3,4,5,6-tetrahydro-2H-pyran-2-one |
| (+)-E-6S-[2-(2-(2-(Cyclohexylmethyl)-4-chloro-6-methyl-phenyl-ethenyl]- | 4R-hydroxy-3,4,5,6-tetrahydro-2H-pyran-2-one |
| (+)-E-6S-[2-(2-(2-(4,4-Dimethylcyclohexylmethyl)-4,6-dimethylphenyl-ethenyl]- | 4R-hydroxy-3,4,5,6-tetrahydro-2H-pyran-2-one |
| (+)-E-6S-[2-(2-(2-(4,4-Dimethylcyclohexylmethyl)-4-methyl-6-chloro-phenyl-ethenyl]- | 4R-hydroxy-3,4,5,6-tetrahydro-2H-pyran-2-one |
| (+)-E-6S-[2-(2-(2-(4,4-Dimethylcyclohexylmethyl)-4-chloro-6-methyl-phenyl-ethenyl]- | 4R-hydroxy-3,4,5,6-tetrahydro-2H-pyran-2-one |
| (+)-E-6S-[2-(2-(2-(4-Fluorobenzyl)-4,6-dimethylphenyl-ethenyl]- | 4R-hydroxy-3,4,5,6-tetrahydro-2H-pyran-2-one |
| (+)-E-6S-[2-(2-(2-(4-Fluorobenzyl)-4,6-dichlorophenyl-ethenyl]- | 4R-hydroxy-3,4,5,6-tetrahydro-2H-pyran-2-one |
| (+)-E-6S-[2-(2-(2-(4-Fluorobenzyl)-4-methyl-6-chloro-phenyl-ethenyl]- | 4R-hydroxy-3,4,5,6-tetrahydro-2H-pyran-2-one |
| (+)-E-6S-[2-(2-(2-(4-Fluorobenzyl)-4-chloro-6-methyl-phenyl-ethenyl]- | 4R-hydroxy-3,4,5,6-tetrahydro-2H-pyran-2-one | mula I with $R^1 = H$ can be esterified with a diazoalkane at temperatures between $-40°$ and $+20°$ C., it being possible to use the customary solvents such as, for example, diethyl ether, tetrahydrofuran, chloroform or lower molecular weight alcohols such as methanol. The resulting esters can be isolated in a straightforward manner by evaporation of the solvent and, where appropriate, can be purified by chromatography. Another method of esterification comprises reacting salts of the dihydroxy acids Ia in the presence of a base, such as, for example, a metal alcoholate or metal carbonate, in a suitable solvent, with an alkylating agent. Examples of suitable metal alcoholates are sodium methylate, sodium ethylate or potassium tertiary-butylate. Examples of suitable solvents are alcohols such as, for example, methanol or tert.-butanol, ethers such as tetrahydrofuran or 1,2-dimethoxyethane and, in particular, dipolar aprotic solvents such as dimethylformamide, dimethyl sulfoxide, acetonitrile or N-methylpyrrolidone. The method of transesterification with an excess of alcohols such as, for example, methanol, ethanol or isopropanol is also suitable for the preparation of esters of the dihydroxy acids.

Where the individual reaction products do not result in a form which is already sufficiently pure for it to be possible to use them for the subsequent reaction step, it is advisable to carry out purification by crystallization, or column, thin-layer or high-pressure liquid chromatography.

BIOLOGICAL ASSAY SYSTEMS

1. HMG-CoA reductase activity in enzyme preparations

The HMG-CoA reductase activity was measured on solubilized enzyme preparations from liver microsomes of rats which, after the day/night rhythm had been changed, were induced with cholestyramine (®Cuemid). The substrate used was (S,R) $^{14}$C-HMG-CoA, and the concentration of NADPH was maintained during the incubation by a regenerating system. $^{14}$C-Mevalonate was removed from the substrate and other products (for example $^{14}$C-HMG) by column elution, the elution profile for each individual sample being determined. Constant inclusion of $^3$H-mevalonate was dispensed with because the determination was of the relative inhibitory effect. In each series of tests, the control containing no enzyme, and the normal mixture containing enzyme (=100%) and those with added products, final concentration $10^{-5}$ to $10^{-9}$M, were treated together. Each individual figure was formed as the mean from 3 parallel samples. The signficance of the differences in the means between samples containing no product and those containing product was assessed by the t test.

Using the method described above, the following figures for the inhibition of HMG-CoA reductase were determined for the compounds according to the invention, for example:

| Example (Tab. 10) | R¹ | R² | R³ | Z | IC$_{50}$ [M] |
|---|---|---|---|---|---|
| 16 g | 4-F-phenyl | H | H | CH$_2$CH$_2$ | $9.0 \times 10^{-7}$ |
| 16 j | cyclohexyl | H | H | CH$_2$ | $9.0 \times 10^{-8}$ |
| 16 l | 4-Cl-phenyl | H | H | CH$_2$ | $8.0 \times 10^{-7}$ |
| 16 y | 4-Cl-phenyl | o-CH$_3$ | H | CH$_2$ | $2.8 \times 10^{-7}$ |
| 16 z | cyclohexyl | o-Cl | p-Cl | CH$_2$ | $1.9 \times 10^{-8}$ |
| 16 u | cyclohexyl | o-CH$_3$ | H | CH$_2$CH$_2$ | $6.5 \times 10^{-7}$ |
| 16 ab | 4-Cl-phenyl | o-Cl | H | CH$_3$ | $2.3 \times 10^{-7}$ |
| 16 ac | cyclohexyl | o-Cl | H | CH$_2$ | $7.1 \times 10^{-8}$ |

2. Suppression or inhibition of HMG-CoA reductase in cell cultures of fibroblasts.

Monolayers of fibroblasts (L cells) in lipoprotein-free nutrient medium were incubated with appropriate concentrations of test substances for a specified period (for example 3 hours) and then the HMG-CoA reductase activity of the cells was determined by modification of the method of Chang et al. (J. Biol. Chem. 256, 6174 (1981)). For this purpose, the cell extracts were incubated with D,L-[$^3$H]-HMG-CoA, and the product [$^3$H]-mevalonate formed from the cells by the action of the HMG-CoA reductase activity present was, after cyclization to [$^3$H]-mevalonolactone, separated from the starting material by thin-layer chromatography and, by use of an internal standard of [$^{14}$C]-mevalonate, the amount of [$^3$H]-mevalonate formed in unit time was determined and related to the amount of cellular protein. The HMG-CoA reductase activity in the cell culture found on addition of a specified concentration of a test product was related, as the percentage, to that of a culture treated in the same way without the test product but with the same solvent concentration.

Testing of substances for
INHIBITION OF HMG-CoA REDUCTASE IN CELL CULTURES
confluent cell culture (monolayer) of HEP-G2 cells

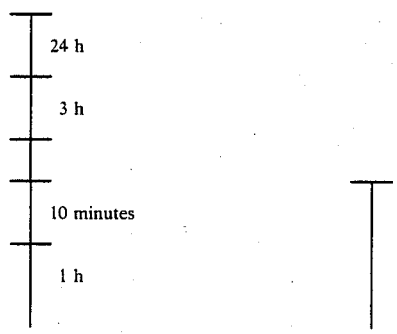

(1.) Lipoprotein-free medium (DMEM) — 24 h (2.) Incubation with test products — 3 h (3.) Cytolysis (4.) Activation of the HMG-CoA reductase present in the cell lysate — 10 minutes (5.) Incubation of the cell lysate with D,L-($^3$H)-HMG-CoA — 1 h

Testing of substances for
INHIBITION OF HMG-CoA REDUCTASE IN CELL CULTURES
confluent cell culture (monolayer) of HEP-G2 cells -continued (6.) Reaction stopped and reaction product cyclized to ($^3$H)-mevalonolactone — 1 h (7.) TLC separation of the reaction product ($^3$H)-mevalonolactone — 1 h (8.) Isolation of the ($^3$H)-mevalonolactone ($^{14}$C)-mevalonate | Internal standard | Cell protein determination (9.) Scintillation measurement and calculation of the proportion of D,L-($^3$H)-HMG-CoA converted to ($^3$H)-mevalonolactone (10.) RESULT:
in nmol of ($^3$H)-mevalonate/mg of cell protein compared with solvent control Using the method described above, the following figures for the inhibition of HMG-CoA reductase (in HEP-G2 cells) were determined for the compounds according to the invention, for example (the IC$_{50}$ (M) is that concentration of the compound which brings about 50% inhibition of HMG-CoA reductase activity):

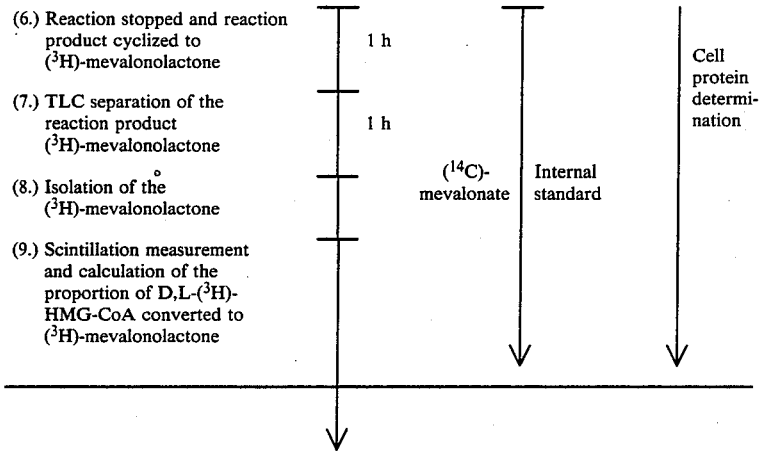

| Example (Tab. 10) | R$^1$ | R$^2$ | R$^3$ | Z | IC$_{50}$ (M) |
|---|---|---|---|---|---|
| 16 g | F-phenyl | H | H | CH$_2$CH$_2$ | 5.0 × 10$^{-4}$ |
| 16 j | cyclohexyl | H | H | CH$_2$ | 3.8 × 10$^{-4}$ |
| 16 z | cyclohexyl | o-Cl | p-Cl | CH$_2$ | 1.9 × 10$^{-6}$ |
| 16 u | cyclohexyl | o-CH$_3$ | H | CH$_2$CH$_2$ | 2.0 × 10$^{-4}$ |
| 16 ab | Cl-phenyl | o-Cl | H | CH$_2$ | 2.1 × 10$^{-4}$ |
| 16 ac | cyclohexyl | o-Cl | H | CH$_2$ | 3.2 × 10$^{-6}$ |
| Mevinolin | | | | | 6.0 × 10$^{-6}$ |

The compounds of the general formula I or Ia are distinguished by potent inhibition of HMG-CoA reductase, the rate-determining enzyme of cholesterol biosynthesis. The enzyme HMG-CoA reductase is widespread in nature. It catalyzes the formation of mevalonic acid from HMG-CoA. This reaction is a central step in cholesterol biosynthesis (cf. J. R. Sabine in CRC Series in Enzyme Biology: 3-hydroxy-3-methylglutaryl-coenzyme-A reductase, CRC Press Inc. Boca Raten, Fla. 1983 (ISBN 0-8493-6551-1)).

High cholesterol levels are regarded as being connected with a number of diseases such as, for example, coronary heart diseases or arteriosclerosis. Hence the reduction of elevated cholesterol levels is an aim of therapy for the prevention and treatment of diseases of this type.

One approach to this is the inhibition or reduction in endogenous cholesterol biosynthesis. Inhibitors of HMG-CoA reductase block cholesterol biosynthesis at an early stage.

Hence the compounds of the general formula I and Ia are suitable as hypolipidemics and for the treatment and prophylaxis of arteriosclerotic changes.

Hence the invention also relates to pharmaceutical products based on these compounds and their use as medicaments, in particular as hypolipidemics and for the prophylaxis of arteriosclerotic changes.

The use of compounds of the formula I or Ia as hypolipidemics or antiarteriosclerotics employs oral doses from 3 to 2,500 mg, but preferably in the dose range 10–500 mg. These daily doses can, as required, also be divided into two to four single doses or administered in controlled release form. The dosage regimen may depend on the type, age, weight, sex and medical condition of the patient.

An additional cholesterol-lowering effect can be achieved by administration of the compounds according to the invention concurrently with substances which bind bile acids, such as, for example, anion exchanger resins. The increased excretion of bile acids results in an enhancement of new synthesis and thus in an increase in cholesterol degradation (cf. M. S. Brown, P. T. Koranen and J. C. Goldstein Science 212, 628 (1981); M.S. Brown, J. C. Goldstein Spektrum der Wissenschaft 1985, 1, 96).

The compounds according to the invention, of the formula I and Ia, can be used in the form of the $\alpha$-lactones, as the free acids, or in the form of their physiologically acceptable inorganic or organic salts or as esters. Acids and salts or esters can be used in the form of their aqueous solutions or suspensions or dissolved or suspended in pharmacologically acceptable organic solvents such as mono- or polyhydric alcohols such as, for example, ethanol, ethylene glycol or glycerol, in triacetin, in alcohol/acetaldehyde diacetal mixtures, oils such as, for example, sunflower oil or fish liver oil, ethers such as, for example, diethylene glycol dimethyl ether or polyethers such as, for example, polyethylene glycol, or in the presence of other pharmacologically acceptable polymeric vehicles such as, for example, polyvinylpyrrolidone or in solid formulations.

Solid presentations which can be administered orally and contain the customary auxiliaries are preferred for the compounds of the formula I and Ia. They are prepared by customary methods.

Tablets, coated tablets or capsules are particularly suitable as formulations for oral use. A dosage unit preferably contains 10 to 500 mg of active compound.

The compounds of the formulae II, III, IV, V and VI are new and represent valuable intermediates for the preparation of compounds of the formula I. Hence the invention also relates to these compounds and to processes for their preparation.

PREPARATION OF THE STARTING COMPOUNDS II

Scheme 1, Z=—CH$_2$—

Example 1

General procedure for the preparation of compounds of the general formula IX (cf. L. A. Walter et al., J. Heterocycl. Chem. 14, 47 (1977)).

Example 1a ($R^2$ and $R^3$=H, $R^1$=2-thienyl)

(2-Thienyl)-2-(methoxymethyl)phenylmethanol IXa

One crystal of iodine was added to 6.34 g (0.26 mol) of magnesium turnings which had been etched with ethereal hydrochloric acid and then thoroughly dried, and the mixture was covered with 60 ml of absolute THF.

50 g (0.25 mol) of 2-methoxymethylbromobenzene (2-bromobenzyl methyl ether (VII) in 500 ml of absolute THF were slowly added dropwise. After the Grignard reaction was complete, 27.9 g (0.25 mol) of 2-thiophenenecarbaldehyde VIII in 200 ml of absolute THF were slowly added dropwise at 50°. The mixture was subsequently heated to reflux for 2 hours. The tetrahydrofuran was then removed by distillation in vacuo. The organic phases were combined, dried with MgSO$_4$, filtered and evaporated in vacuo.

Yield: 60 g 76% of theory of IXa.

Rf=0.42 mobile phase: cyclohexane/ethyl acetate 1:1.

Example 1b–1i

Compounds IXb–Ixi were prepared in a manner analogous to that described in Example Ia (cf. Tab. 1).

Example 2

Procedure for the preparation of compounds of the general formula X-route A

Example 2a ($R^2$ and $R^3$=H, $R^1$=2-thienyl

2-Thienyl-2-(methoxymethyl)phenyl-ketone Xa 46 g (0.2 mol) of (2-thienyl)-2-(methoxymethyl)-phenylmethanol (Example 1a) were dissolved in 380 ml of dioxane and 572 ml of H$_2$O with the addition of 5.72 g of KOH, and the solution was heated to 40° C. While stirring this mixture, 24.94 g (0157 mol) of potassium permanganate were added in smallish portions, awaiting the decolorization of each. After the addition was complete, the mixture was stirred further at 90° C. for 45'. It was then cooled and extracted with 4×200 ml of ether. The organic phases were combined, washed with H$_2$O, dried with MgSO$_4$, concentrated in vacuo and subsequently filtered through silica gel using cyclohexane/ethyl acetate=1:1.

Yield: 34 g 74% of theory of Xa.

Rf=0.57 mobile phase: cyclohexane/ethyl acetate 1:1.

Examples 2c, 2d, 2e, 2g and 2h

Compounds Xc, Xd, Xe, Xg and Xh were prepared in a manner analogous to that described in Example 2a (cf. Tab. 1).

Example 3

Procedure for the preparation of compounds of the general formula XII-route A

Example 3a ($R^2$ and $R^3$=H, $R^1$=2-thienyl)

2-Methoxymethyl-(2-thienyl)benzene XIIa 34 g (0.146 mol) of 2-thienyl 2-(methoxymethyl)phenyl ketone (Example 2a) are dissolved in 232 ml of triethylene glycol together with 41.1 g of KOH. Then 24.68 ml of 91% strength hydrazine are added, and the mixture is heated, with stirring, at 100° C. for 1 hour and at 180° C. for 5 hours. The mixture is then allowed to cool, 400 ml of ice-water are added, and the mixture is extracted with 4×250 ml of ether. The combined ether phases are washed with saturated NaCl solution, dried and concentrated in vacuo. The residue is filtered through $SiO_2$ using cyclohexane/ethyl acetate 9:1.

Yield: 20 g (60% of theory) of XIIa.
Rf=0.61.
Mobile phase: cyclohexane/ethyl acetate 4:1.

Examples 3c, 3d and 3e

Compounds XIIc, XIId and XIIe were prepared in a manner analogous to that described for Example 3a: (cf. Tab. 1)

Example 4

Procedure for the preparation of compounds of the general formula XI-route B.

Example 4g ($R^1$=3,4,5-trimethoxyphenyl, $R^2$ and $R^3$=H)

(2-Methoxymethyl)phenyl-(3,4,5-trimethoxy)phenylacetyloxymethane XIg 34.9 g (0.43 mol) of absolute pyridine were added, under nitrogen at 0°–5° C., to 23 g (0.072 ml) of (2-methoxymethyl)phenyl-(3,4,5-trimethoxy)phenylmethanol (Example 1g) dissolved in 230 ml of absolute $CH_2Cl_2$. Subsequently, while cooling in ice, 10.17 ml (0.144 mol) of acetyl chloride were added dropwise over the course of ¾ h. The mixture was then stirred for ½ hour. The reaction mixture was then poured onto ice and extracted with $CH_2Cl_2$. The organic phase was concentrated. Toluene was added to the residue 3× and residues of pyridine were removed by azeotropic distillation; the product was subsequently dried under high vacuum.

Yield: 26.0 g (~100% of theory) of XIg.
Rf=0.45.
Mobile phase: cyclohexane/ethyl acetate 1:1.

Examples 4b, 4c, 4e, 4f, 4h and 4i

Compounds XIb, XIc, XIe, XIf, XIh and XIi were prepared in a manner analogous to that described in Example 4 g (cf. Tab. 1).

Example 5

Procedure for the preparation of compounds of the general formula XII-route B

Example 5g ($R^1$=3,4,5-trimethoxyphenyl, $R^2$ and $R^3$=H)

2-Methoxymethyl-(3,4,5-trimethoxy)benzylbenzene XIIg 6 g of palladium/barium sulfate were prehydrogenated in 200 ml of absolute MeOH. Then 26 g (0.072 mol) of (2-methoxymethyl)phenyl-(3,4,5-trimethoxy)phenylacetyloxymethane (Example 4 g)+5.92 g (0.072 mol) of sodium acetate were added and hydrogenated. Uptake of $H_2$ was complete after 2 hours. The active charcoal was removed by filtration with suction, under $N_2$, through a filter with a clarifying layer of silica gel. The filtrate was concentrated in vacuo, and the residue was filtered through silica gel using cyclohexane/ethyl acetate 9:1.

Yield: 21 g 96.3% of theory of XIIg.
Rf=0.50.
Mobile phase: cyclohexane/ethyl acetate 1:1.

Examples 5b, 5c, 5f, 5h and 5i

Compounds XIIb, XIIc, XIIf, XIIh and XIIi were prepared in a manner analogous to that described in Example 5 g (cf. Tab. 1).

Example 6

Procedure for the preparation of compounds of the general formula XIII.

Example 6a 2-Thenylbenzyl bromide XIIIa ($R^1$=2-thienyl, $R^2$ and $R^3$=H)

13 g (0.059 mol) of 2-methoxymethyl-(2-thenyl)benzene (Example 3a) were dissolved in 130 ml of 48% strength aqueous hydrobromic acid, and the solution was stirred under reflux for 3 hours.

After cooling, 200 ml of toluene were added, and the mixture was vigorously stirred. The toluene phase was separated off, and the aqueous phase was extracted 2× with toluene. The combined organic phases were washed 1× with ice-water, 1× with saturated $NaHCO_3$ solution and 1× with saturated NaCl solution, and then dried with $MgSO_4$ and concentrated in vacuo. The residue was filtered through silica gel using cyclohexane/ethyl acetate 9:1.

Yield: 15 g (94.3% of theory) of XIIIa Rf=0.63.
Mobile phase: cyclohexane/ethyl acetate 4:1.

Examples 6b–6i

Compounds XIIIb–XIIIi were prepared in a manner analogous to that described for Example 6a (cf. Tab. 1).

TABLE 1

| Example | $R^1$ ($R^2$, $R^3$ = H) | IX Example 1 Rf | IX Example 1 Yield % | Example 2 (route A) Rf | Example 2 (route A) Yield % | XII Example 3 (route A) Rf | XII Example 3 (route A) Yield % | XI Example 4 (route B) Rf | XI Example 4 (route B) Yield % | XII Example 5 (route B) Rf | XII Example 5 (route B) Yield % | XIII Example 6 Rf | XIII Example 6 Yield % |
|---|---|---|---|---|---|---|---|---|---|---|---|---|---|
| a | 2-thienyl | 0.42[(2)] | 76 | 0.57[(2)] | 75 | 0.61[(1)] | 60 | | | | | 0.63[(1)] | 94 |
| b | cyclohexyl | 0.25[(5)] | 84 | | | | | 0.19[(3)] | >95 | 0.48[(3)] | 56 | | 93 |

TABLE 1-continued

| Example | R¹ (R², R³ = H) | IX Example 1 $R_f$ | Yield % | Example 2 (route A) $R_f$ | Yield % | XII Example 3 (route A) $R_f$ | Yield % | XI Example 4 (route B) $R_f$ | Yield % | XII Example 5 (route B) $R_f$ | Yield % | XIII Example 6 $R_f$ | Yield % |
|---|---|---|---|---|---|---|---|---|---|---|---|---|---|
| c | phenyl | 0.40⁽⁵⁾ | 95 | 0.41⁽¹⁾ | 45 | 0.46⁽³⁾ | 89 | 0.36⁽¹⁾ | >95 | 0.46⁽³⁾ | 85 | 0.65⁽³⁾ m.p.: 42–44° C. | |
| d | 4-Cl-phenyl | 0.43⁽⁵⁾ | 70 | 0.47⁽¹⁾ | 57 | 0.40⁽⁴⁾ | 29 | | | — | | 0.65⁽³⁾ m.p.: 53–55° C. | 80 |
| e | 3-CH₃O-phenyl | 0.37⁽²⁾ | 71 | 0.56⁽²⁾ | 32 | 0.45⁽¹⁾ | 73 | 0.25⁽¹⁾ | >95 | | | 0.56⁽¹⁾ | 93 |
| f | 3-F₃C-phenyl | 0.52⁽²⁾ | 76 | | | | | 0.6⁽²⁾ | 100 | 0.46⁽¹⁾ | 17 | 0.55⁽¹⁾ | 77 |
| g | 3,4,5-tri-CH₃O-phenyl | 0.31⁽²⁾ | 87 | 0.46⁽²⁾ | 59 | | | 0.45⁽²⁾ | >15 | 0.50⁽²⁾ | 96 | 0.58⁽²⁾ | 44 |
| h | 4-F-phenyl | 0.42⁽²⁾ | 77 | 0.62⁽²⁾ | 45 | | | 0.25⁽¹⁾ | 89 | 0.52⁽¹⁾ | 63 | 0.63⁽¹⁾ | 82 |
| i | 4-CH₃-phenyl | 0.52⁽⁵⁾ | 95 | | | | | 0.35⁽¹⁾ | >95 | 0.50⁽³⁾ | 87 | 0.60⁽⁴⁾ m.p.: 38–40° C. | 94 |

Mobile phase for thin-layer chromatography:
[1] Cyclohexane/EtOAc = 4:1
[2] Cyclohexane/EtOAc = 1:1
[3] Chloroform
[4] Toluene
[5] Cyclohexane/EtOAc = 9:1

Example 7

Procedure for the preparation of compounds of the general formula II (Z=CH₂)

Example 7a 2-Thenylbenzyltriphenylphosphonium bromide IIa (R¹=2-thienyl, Z=CH₂, R² and R³=H)

15 g (0.056 mol) of 2-thenylbenzyl bromide (Example 6a) are dissolved in 150 ml of absolute toluene, 16.18 g (0.062 mol) of triphenylphosphine are added, and the mixture is heated to reflux for 3 hours. After cooling, the paste of crystals which has formed is removed by filtration through a suction funnel. The residue on the filter is then washed 3× with toluene and 2× with diisopropyl ether, and then the crystals are dried in a vacuum oven at 100° C.

Yield: 24 g (94% of theory) of IIa
$C_{30}H_{20}PSBr$ MW: 529.48.
Melting point 232°–34° C.

Examples 7b–7o

Compounds IIb–IIo (Z=CH₂) were prepared in a manner analogous to that described in Example 7a (cf. Tab. 2).

TABLE 2

$R^1-CH_2-$ phenyl ring with $-CH_2-\overset{+}{P}(C_6H_5)_3$ X⁻, $R^2$, $R^3$ substituents II (Z = CH₂)

| R¹ (R²,R³ = H) | X | Example 7 | Melting point °C. | Yield % |
|---|---|---|---|---|
| 2-thienyl | Br | a | 232–34 | 94 |

TABLE 2-continued $R^1-CH_2-\underset{R^3}{\underset{|}{\overset{CH_2-\overset{+}{P}(C_6H_5)_3\;\; X^-}{\overset{|}{\bigcirc}}}}-R^2 \quad\quad II\;(Z = CH_2)$

| $R^1$ | X | Example 7 | Melting point °C. | Yield % |
|---|---|---|---|---|
| cyclohexyl | Br | b | 196–98 | 95 |
| phenyl | Br | c | 247–49 | 94 |
| 4-Cl-phenyl | Br | d | 224–26 | 90 |
| 3-CH₃O-phenyl | Br | e | 196–97 | 94 |
| 3-F₃C-phenyl | Br | f | 204 | 88 |
| 3,4,5-tri-CH₃O-phenyl | Br | g | 197–99 | 93 |
| 4-F-phenyl | Br | h | 223–25 | 92 |
| 3-CH₃-phenyl | Br | i | 194–95 | 94 |

$R^3 = H$

| $R^1$ | $R^2$ | X | Example 7 | Melting point °C. | Yield % |
|---|---|---|---|---|---|
| cyclohexyl | o-Cl | Cl | k | 205 | 70 |
| 4-Cl-phenyl | o-Cl | Cl | l | 212 | 62 |
| 4-F-phenyl | o-Cl | Cl | m | 253 | 49 |
| 2-CH₃-phenyl | o-CH₃ | Cl | n | 209 | 84 |
| 4-F-phenyl | o-F | Cl | o | 261 | 41 |

Preparation of the starting compounds II (Scheme 2, Z=—CH₂—CH₂—)

Example 8

Procedure for the preparation of the phosphonium salts of the general formula XV (Tab. 3).

Example 8 g 4-Fluorophenyltriphenylphosphonium bromide ($R^1$=4-fluorophenyl, X=Br) XVg 98.6 g (0.52 mol) of 4-fluorobenzyl bromide (XIV, $R^1$=4-fluorophenyl, X=Br) and 136.7 g (0.52 mol) of triphenylphosphine in 400 ml of acetonitrile are boiled under reflux for 6 hours. After cooling, the mixture is concentrated to one half the volume in vacuo, cooled in an ice bath, and the crystals which have separated out are filtered off with suction and washed with cold acetonitrile and diethyl ether. The crystals are thoroughly dried in vacuo at 100° C.

Yield: 223 g of white crystals (95% of theory) of XVg.

Melting point 314° C.

Examples 8a–8k

All the phosphonium salts of the formula XVa–XVk which are listed in Tab. 3 were prepared by the procedure indicated in Example 8 g. The organic halogen compounds XIV (X=Br or Cl) used as starting materials are known.

TABLE 3

$R^1-CH_2-\overset{\oplus}{P}(C_6H_5)_3\;\; X^\ominus \quad\quad XV$

| $R^1$ | X | Example 8 | Melting point °C. | Yield % |
|---|---|---|---|---|
| cyclohexyl | Br | a | 216–17 | 45 |

TABLE 3-continued $$R^1-CH_2-\overset{\oplus}{P}(C_6H_5)_3 \; X^{\ominus} \quad XV$$

| $R^1$ | X | Example 8 | Melting point °C. | Yield % |
|---|---|---|---|---|
|  | Br | b | 300 | 98 |
| 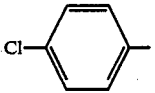 | Cl | c | 284–86 | 57 |
| 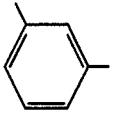 | Cl | d | 297 | 95 |
| 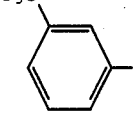 | Cl | e | 290 | 70 |
| 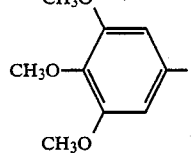 | Cl | f | 235–39 | 89 |
| 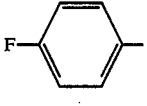 | Br | g | 314 | 95 |
| 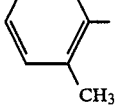 | Cl | h | 273 | 85 |
| 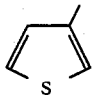 | Br | i | >290 | 63 |
| 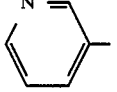 | Cl | k | 250–52 | 50 |

Example 9

Procedure for the preparation of the substituted benzyl halides of the general formula XVII (Tab. 4)

Example 9 g 2-(2-(4-Fluorophenyl)ethenyl)benzyl bromide ($R^1$=4-fluorophenyl, X=Cl) XVIIg 72.14 g (0.16 mol) of 4-fluorophenyltriphenylphosphonium bromide (Example 8 g) are suspended in absolute tetrahydrofuran (300 ml) under $N_2$ at 0° C. At this temperature, 101 ml (0.16 mol) of BuLi in hexane are added dropwise. This results in the formation of a deep red phosphorus ylide. The mixture is stirred for approximately a further 15 min, and then 27.21 g (0.16+0.016 mol) of o-chloromethylbenzaldehyde XVI (prepared by the method of G. Dreyfahl and G. Plötner, Chem. Ber. 94, 907 (1961)) dissolved in 20 ml of absolute THF are added dropwise within 30 min. The mixture is then stirred for about 1 h, the tetrahydrofuran is removed in vacuo, and the residue is extracted several times with a mixture of 500 ml of pentane and 300 ml of $H_2O$. The combined pentane extracts are dried with $MgSO_4$ and concentrated. Active charcoal is added to the residue which is mixed and again extracted with ether (300 ml). The ether extract is separated off and stored in a refrigerator overnight. The ether is decanted off from insolubles, filtered, and concentrated in vacuo. A pale yellow oil remains.

Yield: 37.47 g (95% of theory) of XVIIg.
Rf: 0.5 (E/Z mixture)
in cyclohexane:ethyl acetate=4:1.

Examples 9a–9p

All the substituted benzyl halides of the general formula XVIIa–XVIIp which are listed in Tab. 4 were prepared by the procedure indicated in Example 9 g.

TABLE 4

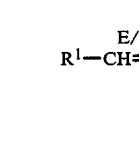

| $R^1$ ($R^2$, $R^3$ = H) | X | Example 9 | Melting point °C. $R_f$ CH/EE= 4:1 | Yield % |
|---|---|---|---|---|
|  | Cl | a | 0.91 | 57 |
| 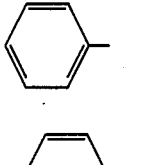 | Cl | b | 0.74 | 85 |
| 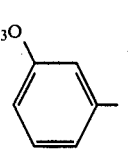 | Cl | c | 0.95 ($CH_2Cl_2$) | 73 |
| 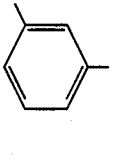 | Cl | d | 0.82 | 72 |
| F₃C- (phenyl) | Cl | e | 0.69 | 77–91 |

TABLE 4-continued $$R^1-\overset{E/Z}{CH=CH}-\underset{R^3}{\overset{CH_2-X}{\bigcirc}}-R^2 \quad XVII$$

| R¹ | | X | Example 9 | Melting point °C. R_f CH/EE= 4:1 | Yield % |
|---|---|---|---|---|---|
| CH₃O-, CH₃O-, CH₃O- (trimethoxyphenyl) | | Cl | f | 0.89 (CH₂Cl₂) | 85 |
| F-phenyl | | Cl | g | 0.5 | 95 |
| o-CH₃-phenyl | | Cl | h | 0.83 | 88/73 |
| 3-methylthiophene | | Cl | i | 0.78 | 63 |

R³ = H

| R¹ | R² | X | Example 9 | Melting point °C. R_f CH/EE= 4:1 | Yield % |
|---|---|---|---|---|---|
| cyclohexyl | o-Cl | Cl | k | 0.91 | 42 |
| 4-Cl-phenyl | o-Cl | Cl | l | 0.82 | 93 |
| 3-CH₃O-phenyl | o-Cl | Cl | m | 0.82 | 65 |
| 3-F₃C-phenyl | o-Cl | Cl | n | 0.69 | 49 |
| 4-F-phenyl | o-F | Cl | o | 0.86 | 95 |
| o-CH₃-phenyl | o-CH₃ | Cl | p | 0.83 | 72 |

Example 10

Procedure for the preparation of the phosphonium salts of the general formula XVIII (Tab. 5)

Example 10 g
2-(2-(4-Fluorophenyl)ethenyl)benzyltriphenylphosphonium bromide (R¹=4fluorophenyl, X=CL)

XVIIIg 37.47 g (0.15 mol) of 2-(2-(4-fluorophenyl)ethenyl)-benzyl bromide (Example 9 g) were dissolved together with 39.3 g (0.15 mol) of triphenylphosphine in 220 ml of xylene, and the solution was heated under reflux for about 3–6 hours. After about ½ hour, the insoluble phosphonium salt which was formed began to separate out. The course of the reaction was followed by thin-layer chromatography on silica gel plates in $CH_3OH/CH_2CL_2=1/1$. After the reaction was complete, the mixture was cooled, the solid salt was filtered off with suction, washed with diethyl ether and dried at 150° C. in vacuo.

Yield: 48.3 g of white crystals (63% of theory) of XVIIIg.

Melting point 225° C.

Examples 10a–10p

All the phosphonium salts of the formula XVIIIa–X-VIIIp listed in Tab. 5 were prepared by the procedure indicated in Example 10 g.

TABLE 5

$$R^1-\overset{E/Z}{CH=CH}-\underset{R^3}{\overset{CH_2-\overset{+}{P}(C_6H_5)_3\overset{-}{X}}{\bigcirc}}-R^2 \quad XVIII$$

| R¹ (R²,R³ = H) | X | Example 10 | Melting point °C. | Yield % |
|---|---|---|---|---|
| cyclohexyl | Cl | a | 282 | 65 |

TABLE 5-continued

| $R^1$ | $R^2$ | X | Example 10 | Melting point °C. | Yield % |
|---|---|---|---|---|---|
| phenyl | | Cl | b | 253 | 66 |
| 4-chlorophenyl | | Cl | c | 193-95 | 47 |
| 3-methoxyphenyl | | Cl | d | 230 | 59 |
| 3-trifluoromethylphenyl | | Cl | e | 210-283 | 61 |
| 3,4,5-trimethoxyphenyl | | Cl | f | >270 | 52 |
| 4-fluorophenyl | | Cl | g | 225 | 63 |
| 2-methylphenyl | | Cl | h | 218 | 50/35 |
| 3-methylthienyl | | Cl | i | oil/crystals | 6 |

$$\begin{array}{c} R^1-CH=CH-\phantom{xx}\overset{E/Z}{\phantom{x}}\phantom{xx}\text{Ar}-CH_2-\overset{+}{P}(C_6H_5)_3 X^- \\ R^3 = H \end{array} \quad \text{XVIII}$$

| $R^1$ | $R^2$ | X | Example 10 | Melting point °C. | Yield % |
|---|---|---|---|---|---|
| cyclohexyl | o—Cl | Cl | k | 215 | 66 |
| 4-chlorophenyl | o—Cl | Cl | l | 255 | 54 |
| 3-methoxyphenyl | o—Cl | Cl | m | 262 | 73 |
| 3-trifluoromethylphenyl | o—Cl | Cl | n | 241 | 85 |
| 4-fluorophenyl | o—Cl | Cl | o | 230 | 61 |
| 2-methylphenyl | o—CH₃ | Cl | p | 219 | 45 |

Example 11

Procedure for the preparation of phosphonium salts of the general formula II (Z=CH₂—CH₂—), Tab. 6.

Example 11g ($R^1$=4-fluorophenyl, X=Cl, Z=CH₂—CH₂)

2-(2-(4-Fluorophenyl)ethyl)benzyltriphenylphosphonium bromide IIg 24.08 g (0.05 mol) of 2-(2-(4-fluorophenyl)ethenyl)-benzyltriphenylphosphonium bromide (Example 10g) are dissolved in 300 ml of absolute methanol and, under nitrogen, 5 g of 10% palladium/animal charcoal are added, and hydrogenation is carried out in a shaken vessel for about 3 hours until the uptake of H₂ is the theoretical figure (0.05 mol of H₂). The mixture is filtered through a filter with a clarifying layer of silica gel which is then washed with methanol. The filtrate is concentrated in vacuo. The remaining oil is dissolved in 50 ml of isopropanol, and the phosphonium salt is precipitated by addition of diethyl ether, and is filtered off with suction and subsequently dried at 150° C. in vacuo.

Yield: 23.3 g of white crystals (91% of theory) of IIg (Z=CH₂—CH₂).

Melting point>159° C.

Examples 11a–11p

All the phosphonium salts of the formula IIa –IIp (Z=—CH₂—CH₂—) listed in Tab. 6 were prepared by the procedure indicated in Example 11g.

TABLE 6

$$R^1-CH_2-CH_2-\text{Ar}(R^2)(R^3)-CH_2-\overset{+}{P}(C_6H_5)_3 X^- \quad II(Z = -CH_2-CH_2-)$$
$R^2, R^3 = H$

| $R^1$ | X | Example 11 | Melting point °C. | Yield % |
|---|---|---|---|---|

TABLE 6-continued

| R¹ | R² | X | Example 11 | Melting point °C. | Yield % |
|---|---|---|---|---|---|
| cyclohexyl | | Cl | a | 241 | 84 |
| phenyl | | Cl | b | 178 | 85 |
| 4-Cl-phenyl | | Cl | c | 200–02 | 68 |
| 3-CH₃O-phenyl | | Cl | d | 269 | 80 |
| 3-F₃C-phenyl | | Cl | e | 265 | 77 |
| 3,4,5-tri-CH₃O-phenyl | | Cl | f | 208–13 | 44 |
| 4-F-phenyl | | Cl | g | >159 | 91 |
| 2-CH₃-phenyl | | Cl | h | 219–290 | 80 |
| 3-methylthiophene | | Cl | i | 110 decomp. | 90 |

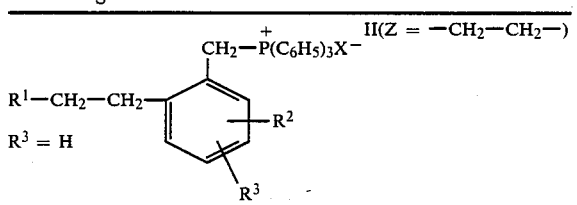

II(Z = —CH₂—CH₂—)

R³ = H

| R¹ | R² | X | Example 11 | Melting point °C. | Yield % |
|---|---|---|---|---|---|
| cyclohexyl | o—Cl | Cl | k | 225 | 80 |
| 4-Cl-phenyl | o—Cl | Cl | l | 231 | 90 |
| 3-CH₃O-phenyl | o—Cl | Cl | m | 282 | 83 |
| 3-F₃C-phenyl | o—Cl | Cl | n | 235 | 81 |
| 4-F-phenyl | o—Cl | Cl | o | 216 | 14 |
| 2-CH₃-phenyl | o—CH₃ | Cl | p | 230 | 70 |

PREPARATION OF THE CHIRAL ALDEHYDE III

Example 12

6S-Formyl-4R-(tert.-butyldiphenyl)silyloxy-2-methoxy-3,4,5,6-tetrahydro-2H-pyran, III

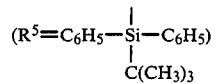

10 g (24.96 mmol) of optically active "Compactin alcohol" ((+)6S-hydroxymethyl-4R-(tert.-butyldiphenyl)silyloxy-2-methoxy-3,4,5,6-tetrahydro-2H-pyran (prepared by the method of Yuh-Ling Yang and J. R. Falck, Tetrahedron Letters Vol. 23, 4305 (1982) were added dropwise at room temperature to a stirred mixture of 25 g (0.125 mol) of chromium trioxide in 965 ml of absolute $CH_2Cl_2$ and 39.5 g (0.5 mol) of absolute pyridine, which had been prepared at 0° C., within 30', and the mixture was stirred for a further 30'. The contents of the flask were then rapidly filtered with suction through a clarifying layer of silica gel. The clear filtrate was concentrated in vacuo.

Yield: 9.46 g (95% of theory) of III.

$R_f$: 0.10.

Mobile phase: cyclohexane:ethyl acetate=4:1.

$C_{23}H_{30}SiO_4$ (398.6) ¹H NMR, 60 MHz: —CH=O $\delta$=9.65 ppm, in $CDCl_3$ —$OCH_3$ $\delta$=3.5 ppm.

PREPARATION OF THE FINAL PRODUCTS I AND IA

Example 13

E/Z isomers

6S-[2-(2-(2-(4-Fluorophenyl)ethyl)phenyl)ethenyl]-4R-(tert.-butyldiphenyl)silyloxy-2-methoxy-3,4,5,6-tetrahydro-2H-pyran, IVg Tab. 7

($R^1$=4-fluorophenyl, $R^2$ and $R^3$=H, $R^5$=

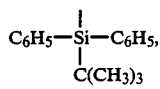

$Z=(CH_2)_2 Z=(CH_2)_2$ 7.9 g (15.5 mol) of 2-(2-(4-fluorophenyl)ethyl)benzyl-triphenylphosphonium bromide (Example 11g) were dried at 100° C. under high vacuum and, with exclusion of moisture, were suspended in 67 ml of absolute THF. At 0° C., 9.7 ml (15.5 mmol) of butyllithium in hexane were added dropwise. The mixture was stirred at 0° C. for about 30 minutes. Then, likewise at 0° C., 6.12 g (15.35 mmol) of 6S-formyl-4R-(tert.-butyldiphenyl)-silyloxy-2-methoxy-3,4,5,6-tetrahydro-2H-pyran (Example 12) in 15 ml of absolute tetrahydrofuran were added dropwise. After stirring at room temperature for 1 hour, THF was removed by evaporation in vacuo, the residue was taken up in ethyl acetate, and the solution was extracted several times with water, dried over MgSO₄, filtered and concentrated. The residue was fractionated into the pure E and Z isomers by chromatography on a silica gel column (for example, Merck Lobar ® size C) using cyclohexane/ethyl acetate 40:1.

| Yield: | 1st fraction | 45–230 = | 4.0 g of E isomer |
|---|---|---|---|
| | 2nd fraction | 231–280 = | 2.1 g of Z isomer |
| | | | 6.1 g of pale oil |
| | | | (68% of theory) IV g |

E isomer of IVg: $R_f$=0.64 cyclohexane/ethyl acetate=4:1.

NMR in CDCl₃ δ values in ppm: 1.1 (s, 9H)C(CH₃)₃; 1.2–1.9(m, 4H)CH₂; 2.8–3.0(m, 4H)CH₂CH₂; 3.58(s, 3H)OCH₃; 4.3–4.35(m, 1H)>CH-OSi; 4.65–4.85(m, 1H) >CHOCH₃; 4.97(dd, 1H)>CHOCO; 6.12(dd, J=16 Hz, 1H)—CH=; 6.85 (d, J=16 Hz, 1H)—CH=; 7.0–7.8(m, 8H)aromat. prot.

Z isomer of IVg: $R_f$=0.56 cyclohexane/ethyl acetate=4:1.

NMR in CDCl₃ δ values in ppm: 0.95(s, 9H) C(CH₃)₃; 1.2–1.9(m, 4H) CH₂; 2.7–2.8(m, 4H)CH₂CH₂; 3.45(s, 3H)OCH₃; 4.2–4.3(m, 1H)>CH—OSi; 4.65–4.85(m, 1H)>CHOCH₃; 4.75(dd, 1H)>CHOCO; 5.8(dd, J=10 Hz, 1H) —CH=; 6.65 (d, J=10 Hz, 1H)—CH=; 7.05–7.8(m, 8H)aromat. Prot.

Examples 13a–13r

In a manner analogous to that described in Example 13 for compound IVg, compounds IVa–IVi (Tab. 7, Z=CH₂CH₂—) were prepared from the aldehyde III (Example 12) and the phosphonium salts II (Tab. 6), and the compounds IVj–IVr (Tab. 7, Z=CH₂) were prepared from the aldehyde III (Example 12) and the phosphonium salts II (Tab. 2).

TABLE 7

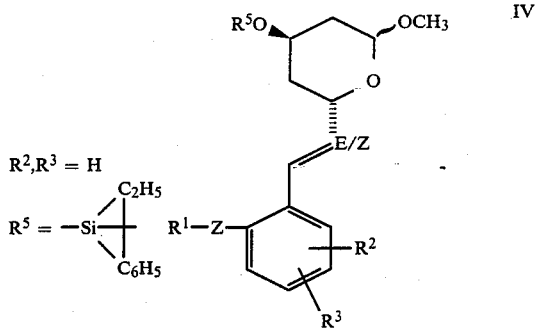

| $R^1$ | Z | Example 13 | $R_f^1$ E/Z | Yield % |
|---|---|---|---|---|
| cyclohexyl | —CH₂—CH₂ | a | 0.74/0.69 | 90 |
| phenyl | CH₂—CH₂ | b | 0.73/0.63 | 95 |
| 4-Cl-phenyl | CH₂—CH₂ | c | 0.71/0.60 | 88 |
| 3-CH₃O-phenyl | CH₂—CH₂ | d | 0.54/0.44 | 83 |
| 3-F₃C-phenyl | CH₂—CH₂ | e | 0.77/0.62 | 60 |
| 3,4,5-tri-CH₃O-phenyl | CH₂—CH₂ | f | 0.69/0.60 | 72 |
| 4-F-phenyl | CH₂—CH₂ | g | 0.64/0.56 | 68 |
| 2-CH₃-phenyl | CH₂—CH₂ | h | 0.72/0.61 | 85 |

TABLE 7-continued

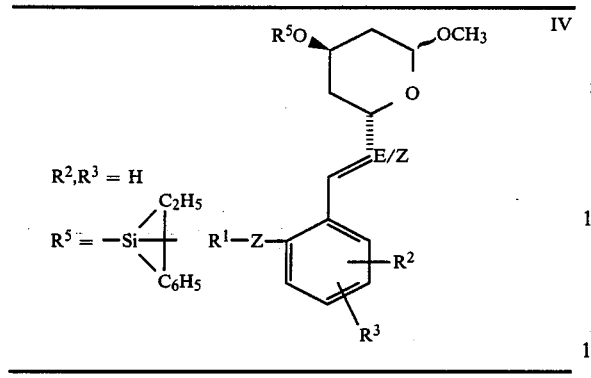

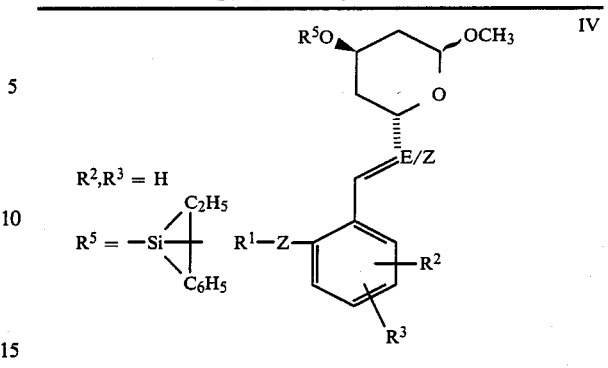

| R[1] | Z | Example 13 | R_f[1] E/Z | Yield % |
|---|---|---|---|---|
| 3-thienyl | CH₂—CH₂ | i | 0.59/0.50 | 72 |
| cyclohexyl | CH₂ | j | 0.27/0.18[4] | 77 |
| phenyl | CH₂ | k | 0.33/0.25[2] | 88 |
| 4-Cl-phenyl | CH₂ | l | 0.29/0.20[3] | 79 |
| 4-CH₃O-phenyl | CH₂ | m | 0.43/0.37[1] | 86 |
| 3-F₃C-phenyl | CH₂ | n | 0.65/0.58[1] | 82 |
| 3,4,5-tri-CH₃O-phenyl | CH₂ | o | 0.25/0.19[1] | 81 |
| 4-F-phenyl | CH₂ | p | 0.52/0.46[1] | 80 |
| 3-CH₃-phenyl | CH₂ | q | 0.33/0.25[3] | 82 |
| 2-thienyl | CH₂ | r | 0.53/0.47[1] | 71 |

[1]Cyclohexane/EtOAc 4:1
[2]Cyclohexane/EtOAc 5:1
[3]Cyclohexame/EtOAc 9:1
[4]Toluene

Example 14

E/Z isomers

6S-[2-(2-(2-(4-Fluorophenyl)ethyl)phenyl)ethenyl]-4R-(tert.-butyldiphenyl)silyloxy-2-hydroxy-3,4,5,6-tetrahydro-2H-pyran Vg (Tab. 8)

($R^1$=4-fluorophenyl, $R^2$ and $R^3$=H, $R^5$=

$$\begin{array}{c} C_6H_5SiC_6H_5 \\ | \\ C(CH_3)_3 \end{array}$$

Z=(CH₂)₂)

3.7 g (6.4 mmol) of compound IVg (Example 13g) are dissolved in 13 ml of tetrahydrofuran, and then 13 ml of water and 19 ml of glacial acetic acid are added. The mixture is stirred at 70° C. for about 5 hours, the tetrahydrofuran is removed in vacuo, 30 ml of toluene are added to the residue, and the mixture is again concentrated in vacuo for azeotropic removal of residues of glacial acetic acid.

Yield: 3.6 g (98% of theory) of Vg.
$C_{37}H_{41}O_3SiF$ MW: 580.

| $R_f$ = 0.35 E isomer | Mobile phase: | cyclohexane/ethyl acetate = 4:1 |
| $R_f$ = 0.25 Z isomer | | |

Examples 14a–14r

In a manner analogous to that described for Vg in Example 14, the compounds Va–Vr (Tab. 8) were prepared. It is possible to use as starting compounds the corresponding compounds IVa–IVr (Tab. 7) in the form of the pure E or Z isomers or as mixtures of the E/Z isomers.

TABLE 8

$R^2, R^3 = H$ $R^5 = -\underset{\underset{C_6H_5}{|}}{\overset{\overset{C_6H_5}{|}}{Si}}+$ Structure V:

(pyranose ring with $R^5O$ and OH substituents, connected via E/Z vinyl to phenyl bearing $R^1-Z$, $R^2$, $R^3$)

| $R^1$ | Z | Example 14 | $R_f^1$ E/Z | Yield % |
|---|---|---|---|---|
| cyclohexyl | CH₂CH₂ | a | 0.36/0.25 | 89 |
| phenyl | CH₂CH₂ | b | 0.32/0.23 | 91 |
| 4-Cl-phenyl | CH₂CH₂ | c | 0.39 | 96 |
| 3-CH₃O-phenyl | CH₂CH₂ | d | 0.33 | 95 |
| 3-F₃C-phenyl | CH₂CH₂ | e | 0.45 | 93 |
| 3,4,5-tri-CH₃O-phenyl | CH₂CH₂ | f | 0.42 | 80 |
| 4-F-phenyl | CH₂CH₂ | g | 0.35/0.25 | 98 |
| 2-CH₃-phenyl | CH₂CH₂ | h | 0.40/0.36 | 72 |
| thien-3-yl | CH₂CH₂ | i | 0.36/0.28 | 68 |

TABLE 8-continued

| $R^1$ | Z | Example 14 | $R_f^1$ | Yield % |
|---|---|---|---|---|
| cyclohexyl | CH₂ | j | 0.26 | 75 |
| phenyl | CH₂ | k | 0.08² | 97 |
| 4-Cl-phenyl | CH₂ | l | 0.16¹ | 97 |
| 3-CH₃O-phenyl | CH₂ | m | 0.30¹ | 90 |
| 3-F₃C-phenyl | CH₂ | n | 0.30¹ | 88 |
| 3,4,5-tri-CH₃O-phenyl | CH₂ | o | 0.21¹ | 85 |
| 4-F-phenyl | CH₂ | p | 0.30¹ | 97 |
| 3-CH₃-phenyl | CH₂ | q | 0.11² | 81 |
| thien-2-yl | CH₂ | r | 0.21¹ | 68 |

[1] Cyclohexane/EtOAc 4:1
[2] Cyclohexane/EtOAc 5:1

E

Example 15

E/Z isomers

6S-[2-(2-(2-(4-Fluorophenyl)ethyl)phenyl)ethenyl]-4R-(tert.-butyldiphenyl)silyloxy-3,4,5,6-tetrahydro-2H-pyran-2-one VIg (Tab. 9)

($R^1$=4-fluorophenyl, $R^2$ and $R^3$=H, $R^5$=

$$\begin{array}{c} C_6H_5SiC_6H_5 \\ | \\ C(CH_3)_3 \end{array}$$

Z=$(CH_2)_2$)

2.88 g (28.8 mmol) of chromium trioxide are introduced into 306 ml of absolute methylene chloride and stirred at 0° C. until a suspension of a fine powder is obtained. Then 4.55 g (57.6 mmol) of absolute pyridine in 10 ml of absolute methylene chloride are added dropwise. The orange-yellow solution is stirred for 20 minutes. Subsequently, 1.67 g (2.88 mmol) of compound Vg (Example 14), dissolved in 10 ml of absolute methylene chloride, are added dropwise. The mixture is then stirred at room temperature for 30'. The reaction solution is filtered with suction through a clarifying layer of silica gel and MgSO$_4$, and the filtrate is concentrated in vacuo.

Yield: 1.52 g (92% of theory) (E/Z isomers) of VIg. $C_{37}H_{39}O_3FSi$ MW: 578.

| | | |
|---|---|---|
| $R_f$ = 0.33 E isomer | Mobile phase: | cyclohexane/ethyl acetate = 4:1 |
| $R_f$ = 0.28 Z isomer | | |

To prepare the pure E (trans) isomer of the compound VIg, 0.52 g of the mixture of E/Z isomers of VIg was dissolved in 10 ml of toluene, 52 mg of iodine were added, and the mixture was subsequently heated to reflux for 48 hours. After removal of the toluene in vacuo and filtration of the residue through silica gel (mobile phase: cyclohexane/ethyl acetate=4:1), the E isomer VIg was obtained.

Yield: 0.48 g VIg E isomer (93% of theory).

$R_f$=0.33 (cyclohexane/ethyl acetate 4:1).

$^1$H NMR, 270 MHz, δ values in ppm: 1.1 (s, 9H)—C(CH$_3$)$_3$; 1.5–2.7(m, 4H), CH$_2$; 2.75–3.0(m, 4H)CH$_2$CH$_2$; 4.3–4.4(m, 1H), >CHOSi; 5.35–5.45(m, 1H)>CHOCO; 6.0(dd, J=16 H$_2$, 1H)—CH═; 6.85(d, J=16 Hz, 1H)—CH═; 6.9–7.7(m, 8H) aromat. Prot.

Examples 15a–15r

In a manner analogous to that described in Example 15 for compound VIg, compounds VIa–VIr (Tab. 9) were prepared. It is possible to use as starting compounds the corresponding compounds Va–Vr (Tab. 8) in the form of the pure E or Z isomers or as mixtures of E/Z isomers. The pure E isomers are readily obtained as described above by isomerization of the E/Z isomer mixtures in the presence of iodine, or by separation by chromatography.

TABLE 9

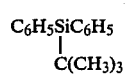

VI $R^2, R^3 = H$ $R^5 = -Si\begin{pmatrix}C_2H_5\\C_6H_5\end{pmatrix}$ $R^1-Z-$

| $R^1$ | Z | Example 15 | $R_f^1$ E/Z | Yield % |
|---|---|---|---|---|
| | | | E/Z | % |
| cyclohexyl | CH$_2$CH$_2$ | a | 0.34/0.30 | 70 |
| phenyl | CH$_2$CH$_2$ | b | 0.43/0.39 | 58 |
| Cl—C$_6$H$_4$— | CH$_2$CH$_2$ | c | 0.29/0.23 | 89 |
| CH$_3$O—C$_6$H$_4$— | CH$_2$CH$_2$ | d | 0.23 | 82 |
| F$_3$C—C$_6$H$_4$— | CH$_2$CH$_2$ | e | 0.59 | 73 |
| 3,4,5-(CH$_3$O)$_3$C$_6$H$_2$— | CH$_2$CH$_2$ | f | 0.50 | 60 |
| F—C$_6$H$_4$— | CH$_2$CH$_2$ | g | 0.33/0.28 | 92 |
| 2-CH$_3$—C$_6$H$_4$— | CH$_2$CH$_2$ | h | 0.41 | 58 |
| 3-thienyl | CH$_2$CH$_2$ | i | 0.50/0.44 | 45 |

TABLE 9-continued

Structure VI: R²,R³ = H; R⁵ = −Si(C₂H₅)(C₆H₅)(−); with R¹−Z− attached to phenyl bearing R², R³

| R¹ | Z | Example 15 | $R_f$ E/Z | Yield % |
|---|---|---|---|---|
| cyclohexyl | CH₂ | j | 0.26[1] | 68 |
| phenyl | CH₂ | k | 0.37/0.31[1] | 93 |
| 4-Cl-C₆H₄ | CH₂ | l | 0.23[2] | 87 |
| 3-CH₃O-C₆H₄ | CH₂ | m | 0.25[1] | 60 |
| 3-F₃C-C₆H₄ | CH₂ | n | 0.27[1] | 75 |
| 3,4,5-(CH₃O)₃-C₆H₂ | CH₂ | o | 0.13[1] | 69 |
| 4-F-C₆H₄ | CH₂ | p | 0.28[1] | 92 |
| 3-CH₃-C₆H₄ | CH₂ | q | 0.17[2] | 70 |
| 2-thienyl | CH₂ | r | 0.25[1] | 70 |

[1] Cyclohexane/EtOAc 4:1
[2] Cyclohexane/EtOAc 5:1

Example 16

Preparation of optically pure compounds of the general formula I:
(+)-E-6S-[2-(2-(2-(4-fluorophenyl)ethyl)phenyl)ethenyl]-4R-hydroxy-3,4,5,6-tetrahydro-2H-pyran-2-one Ig Tab. 10

(R¹=4-Fluorophenyl, R² and R³=H, A-B=CH=CH, Z=CH₂—CH₂)

0.1 ml (1.7 mmol) of glacial acetic acid and 0.39 g (1.24 mmol) of tetrabutylammonium fluoride.3H₂O are added to 0.48 g (0.83 mmol) of compound VIg (E isomer) (Example 15 g). The mixture is stirred at 20° C. for about 5 hours. Then the solvent is removed in vacuo, and the residue is taken up in diethyl ether. The organic phase is extracted 1× with water and 1× with saturated NaHCO₃ solution, and is then dried over MgSO₄, filtered and concentrated in vacuo. Chromatography on a silica gel column (for example, Merck Lobar ®) with cyclohexane/ethyl acetate=1:1 provided:

Yield: 0.26 g (92.1% of theory) of Ig.
$C_{21}H_{21}O_3F$: MW: 340.
$R_f$=0.22 (cyclohexane/ethyl acetate 1:1).
¹H NMR 270 MHz: δ values in ppm: (cf.: Tab. 10).
Specific optical rotation in absolute methanol: $[\alpha]_{CH_3OH}$=21.5°.

Examples: 16a–16ae

In a manner analogous to that described in Example 16 for compound Ig, compounds I (Tab. 10) were prepared.

Where precursors of the final products listed in Tab. 10 have not been described, they were obtained in a manner analogous to that explained in the preceding Examples.

TABLE 10

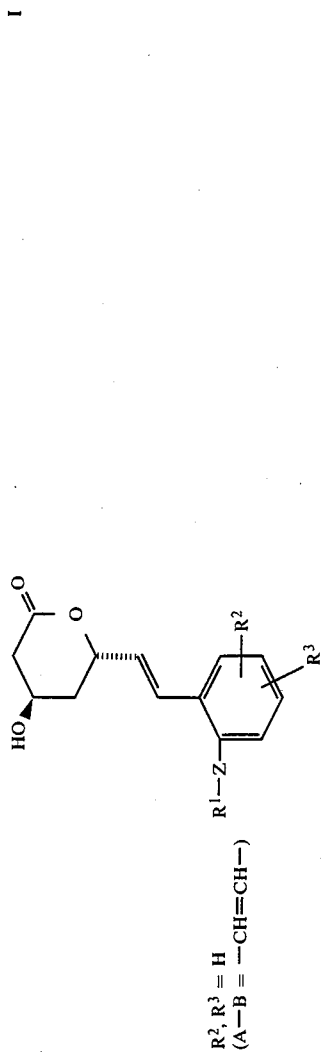

R², R³ = H
(A—B = —CH=CH—)

| R¹ | Z | Example 16 | R_f E | Yield % | ¹H NMR 270 MHz δ values in ppm | Mass spectrum |
|---|---|---|---|---|---|---|
| cyclohexyl | CH₂—CH₂ | a | 0.18 | 72 | | $C_{21}H_{28}O_3$ M=328 |
| phenyl | CH₂—CH₂ | b | 0.27 | 68 | | $C_{21}H_{22}O_3$ M=322 |
| 4-Cl-phenyl | CH₂—CH₂ | c | 0.28 | 76 | 1.6–1.7(broad, s, 1H, OH); 1.9–2.15(m, 2H)CH₂;2.6–3.1(m, 6H)CH₂CH₂CH₂;4.4–4.5(m²1H)CHCH;5.3–5.4(m, 1H)CHOCOO; 6.1(dd, J=16Hz, 1H)CH=;6.9(d, J=16Hz, 1H); 7.0–7.5(m, 8H)aromat. prot. | $C_{21}H_{21}O_3Cl$ M=356 |
| 3-CH₃O-phenyl | CH₂—CH₂ | d | 0.19 | 59 | 1.6–1.9 broad s, 1H, OH); 1.9–2.15(m, 2H)CH₂;2.6–3.0(m, 6H) CH₂CH₂,CH₂;3.8(s, 3H)OCH₃;4.4–4.5(m, 1H)>CH—OH;5.3–5.4(m, 1H) CHOCO;6.1(dd, J=16Hz, 1H)CH=;6.9 (d, J=16Hz, 1H);6.7-7.5(m, 8H) aromat. Prot. | $C_{22}H_{24}O_4$ M=352 |
| 3-F₃C-phenyl | CH₂—CH₂ | e | 0.23 | 62 | 1.9–2.2(m, 3H)CH₂CH₂OH;2.6–3.0(m, 6H)CH₂CH₂CH₂;4.4–4.5(m, 1H) >CHOH;5.3–5.4(m, 1H)>CHOCO;6.1 (dd, J=16Hz, 1H)CH=;6.9(d, J=16Hz, 1H)CH=;7.05–7.5(m, 8H) arom. prot. | $C_{22}H_{21}F_3O_3$ M=390 |

TABLE 10-continued

| | | | | | |
|---|---|---|---|---|---|
| f | CH₃O-⟨benzene with 3,4,5-OCH₃⟩ | CH₂—CH₂ | | 49 | C₂₄H₂₈O₆ M=412 |
| g | ⟨fluorobenzene⟩ | CH₂—CH₂ | 0.22 [α]_D = +21.5° CH₃OH | 70 | C₂₁H₂₁FO₃ M=340  1.5–1.7(broad s, 1H)OH;1.9– 2.2(m, 2H)CH₂;2.6–3.0(m, 6H) CH₂CH₂, CH₂;4.4–4.5(m, 1H)>CH— OH;5.28–5.4(m, 1H)>CHOCO;6.08 (dd, J=16Hz, 1H)CH=;6.9(d, J=16 Hz, 1H)CH=;6.95–7.5(m, 8H) aromat. protons |
| h | ⟨toluene, CH₃⟩ | CH₂—CH₂ | 0.24 | 68 | C₁₂H₂₄O₃ M=366 |
| i | ⟨thiophene, S⟩ | CH₂—CH₂ | 0.16 | 52 | C₁₉H₂₀O₃ M=328 |

¹ Cyclohexane/EtOAc 1:1

Example 16

⟨Structure: pyranone ring with HO substituent, linked via CH=CH to substituted benzene bearing R¹—Z, R², R³⟩

R², R³ = H
(A—B = —CH=CH—)

| R¹ | Z | R_f¹ m.p. °C. E | Yield % | ¹H NMR 279 MHz δ values in ppm | Mass spectrum |
|---|---|---|---|---|---|

TABLE 10-continued

| | | | | |
|---|---|---|---|---|
|  | CH$_2$ | j | 0.18[1] | 4.4-4.5(m, 1H)CHCH;5.3-5.4(m, 1H)CHCH 6.1(dd, J=16Hz, 1H)CH=; 6.95(d,H=16Hz, 1H)CH=;7.1-7.5(m,4H)aromat. prot. | C$_{20}$H$_{26}$O$_3$ M=314 |
| 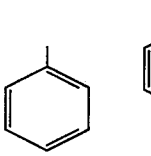 | CH$_2$ | k | E:0.13[4] m.p. θ8-101° C. Z:0.16[1] 73-76° C. | 1.8-2.1 (m, 3H)CH$_2$, =H;2.5-2.8(m,2H) CH$_2$;4.05(s, 2H)CH$_2$;4.25(m,1H)>CH—OH 5.2-5.35(m,1H)>CHOCO;6.02(dd, J=16 Hz,1H(CH=;6.88(d, J=16Hz,1H)CH=; 7.05-7.5(m, 8H) aromat. protons | C$_{20}$H$_{20}$O$_3$ M=308 |
| 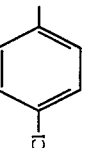 | CH$_2$ | l | 0.16[1] m.p. 100-102° C. | 1.75-2.1(m, 3H)CH$_2$, OH;2.55-2.8 (m, 2H)CH$_2$;4.0(s, 2H)CH$_2$;4.28- 4.35(m, 1H)>CH—OH;5.2-5.3(m,1H) >CHOCO;6.0(dd, J=16Hz, 1H)CH=; 6.8(d, J=16Hz, 1H)CH=;7.0-7.5(m 8H) aromat. protons | C$_{20}$H$_{19}$ClO$_3$ M=342 |
| 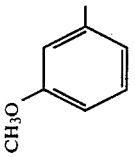 | CH$_2$ | m | 0.12[1] | 3.8(s, 3H)OCH$_3$ | C$_{21}$H$_{22}$O$_4$ M=338 |
| 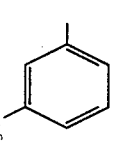 | CH$_2$ | n | 0.13[1] m.p. 86-87° C. | 1.8-2.05(m, 3H)CH$_2$, OH;2.6-2.8 (m,2H)CH$_2$;4.1(s, 2H)CH$_2$;4.3-4.4(m, 1H >CHOH;5.2-5.32(m, 1H)>CHOCO;6.02(dd, 16Hz, 1H)CH=; 6.85(d, 16Hz, 1H)CH=;7.1-7.5(m, 4H) aromat. protons | C$_{21}$H$_{11}$F$_3$O$_3$ M=376 |
| 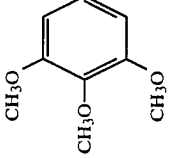 | CH$_2$ | o | 0.38[2] m.p. 90-81 | 1.75-2.05(m, 3H)CH$_2$,CH$_2$;2.5-2.8(m, 2H) CH$_2$;3.78(s, 2H)CH$_2$;4.22-4.31(m, 1H) >CHOH;5.2-5.32(m, 1H)>CHOCO;6.0(dd, 16Hz, 1H)CH=;6.3(s, 2H)aromat. prot.; 6.85(d, 16Hz, 1H)CH=;7.1-7.5(m, 4H) aromat. prot. | C$_{23}$H$_{26}$O$_6$ M=398 |
| 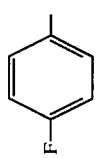 | CH$_2$ | p | 0.51[2] m.p. 108-109 | 1.5-1.7(broad s, CH);1.8-2.05(m, 2H)CH$_2$;2.55-2.8(m, 2H)CH$_2$;4.03)s, 2H)CH$_2$;4.3-4.4(m, 1H)>CH—OH;5.2-5.35 (m, 1H)>CH—OCO;6.02(dd, J=16Hz, 1H) CH=;6.85(d, J=16Hz, 1H)CH=;6.9-7.5 (m, 8H)aromat. prot. | C$_{20}$H$_{19}$O$_3$ M=326 |

TABLE 10-continued

| R¹ | R² | R³ | Z | | Rf¹/rotation | Yield % | ¹H NMR 270 MHz δ-values in ppm | Mass spectrum melting point |
|---|---|---|---|---|---|---|---|---|
| (3-CH₃-phenyl) | CH₂ | | | q | 0.11⁴ m.p. 105-106 | 92 | 1.5-1.7(broad s, 1H)CH;1.8-2.1(m, 2H(CH₂);2.28(s, 3H)CH₃;2.5-2.8(m, 2H)CH₂;4.0(s, 2H)CH₂;4.3-4.4(m, 1H)>CHOH 5.25-5.35(m, 1H)CHOCO;6.05(dd, J=16 Hz, 1H)CH=;6.85-7.5(m, 9H)CH=;aromat. prot. | C₂₁H₂₂O₃ M=322 |
| (2-methylthiophene) | CH₂ | | | r | 0.12¹ | 68 | 1.7-2.05(m, 3H)CH₂,OH;2.5-2.8(m, 1H)CH₂;4.12(s, 2H)CH₂;4.25-4.35(m, 1H) >CHOH;5.2-5.3(m, 1H)>CHOCO;6.0(dd, J=16Hz, 1H)CH=;6.6-7.45(m, 9H)CH=; aromat. prot. | C₁₈H₁₈O₃ M=314 |

¹Cyclohexane(EtOAc = 1:1)
²EtOAc
³n-Hexane/EtOAc
⁴CHCl₃/EtOAc = 9:1

(A—B = CH=CH—) R¹—Z—[structure with R², R³ on phenyl, connected via CH=CH to tetrahydropyranone with OH]

| | R¹ | R² | R³ | Z | | Rf¹/rotation | Yield % | ¹H NMR 270 MHz δ-values in ppm | Mass spectrum melting point |
|---|---|---|---|---|---|---|---|---|---|
| Example 16 | (4-F-phenyl) | o-Cl | H | CH₂CH₂ | s | 0.38 [α]D = +17.4° CH₃CH (C=1) | 61 | 1.5-1.9(broad s, 1H) OH;1.9-2.2(m, 2H)CH₂; 2.65-3.0(m, 6H)CH₂—CH₂, CH₂;4.43-4.40(m, 1H) CH—OH;5.34-5.42(m, 1H) CHOCO;5.85(dd, J=16, 1H)CH=;6.9-7.3(m, 7H) aromat. prot. | C₂₁H₂₀O₃ClF 374.5 M.p.: 86-88° C. |

TABLE 10-continued

| | | | | | | |
|---|---|---|---|---|---|---|
| Ar | R | | | | NMR | Formula / MW / M.p. |
| o-CH₃ phenyl | H | CH₂CH₂ | t | 58 | 0.30 [α]= +25.6° CH₃OH (C=1) | 1.6(broad s, 1H)OH; 1.85-2.2(m, 2H)CH₂;2.28 (s, 3H)CH₃;2.6-3.0(m, 6H) CH₂—CH₂,CH₂;4.38-4.45 (m, 1H)>CH—OH;5.32-5.41 (m, 1H)CHOCO;5.68(dd, J=16Hz, 1H)CH=;6.68 (d, J=16Hz, 1H)CH=;7.05-7.30(m, 8H)aromat. prot. | C₂₂H₂₄O₃ 337.1 M.p.: 97° C. |
| o-CH₃ cyclohexyl | H | CH₂CH₂ | u | 43 | 0.43 [α]= +29.4° CH₃OH (C=1) | 0.85-2.2(m, 16H)Cyclo-hexyl, CH₂, OH);2.29(s, 3H)CH₃;2.55-2.9(m, 4H) CH₂,CH₂;4.45-4.52(m, 1H)CHOCO;5.7(dd, J= 16Hz, 1H(CH=;6.72(d, J= 16Hz, 1H)CH=;7.0-7.2(m, 3H) aromat. prot. | C₂₂H₃₀O₃ 343.12 M.p.: 89° C. |
| o-Cl cyclohexyl | H | CH₂CH₂ | v | 38 | 0.45 | 0.85-2.2(m, 16H)Cyclo-hexyl, CH₂, OH);2.6-2.65(m, 4H)CH₂,CH₂;4.45-4.55(m, 1H)CHOH;5.35-5.45(m, 1H)CHOCO;5.68-69° C. (dd, J=16Hz, 1H)CH=; 7.05-7.25(m, 3H)aromat. prot. | C₂₂H₂₇O₃Cl 363.57 M.p.: 68°-69° C. |
| o-Cl phenyl | H | CH₂CH₂ | w | 34 | 0.40 | 1.6(broad s, 1H)OH; 1.9-2.2(m, 2H)CH₂;2.6-3.0(m, OH)CH₂—CH₂,CH₂; 4.4-4.5(m, 1H)CHOH; 5.3-5.4(m, 1H)CHOCO; 5.82(dd, J=16Hz, 1H) CH=;6.6(d, J=16Hz, 1H) CH=;7.05-7.26(m, 7H) aromat. prot. | C₂₁H₂₀O₃Cl₂ 391.96 M.p.: 102° C. |
| o-Cl cyclohexyl | p-Cl | CH₂CH₂ | x | 45 | 0.4 | 0.85-2.2(m, 16H)Cyclo-hexyl, CH₂, OH;2.6-2.94 (m, 4H)CH₂, CH₂;4.4-4.56(m, 1H)CHOH;5.35-5.45(m, 1H)CHOCO;5.87 (dd, J=16Hz, 1H)CH=;6.58 (d, 1H);7.26(d, 1H) aromat. prot. | C₂₁H₂₆O₃Cl₂ 398.02 |

TABLE 10-continued

| | | | | | | |
|---|---|---|---|---|---|---|
| 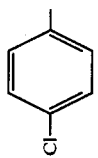 | o-CH₃ | H | CH₂ | y | 0.23 | 89 | 1.7(broad s, 1H)OH; 1.7–2.05(m, 2H)CH₂;2.29 (s, 3H)CH₃;2.6–2.8(m, 2H)CH₂;3.95(s, 2H)CH₂; 4.3–4.4(m, 1H)CHOH;5.2– 5.35(m, 1H)CHOCO;5.6 (dd, J=16Hz, 1H)CH=; 6.6(d, J=16Hz, 1H)CH=; 6.95–7.28(m, 7H)aromat. prot. | C₂₁H₂₁ClO₃ 356.8 M.P.: 83–85° C. |
|  | o-Cl | p-Cl | CH₂ | z | 0.22 | 86 | 0.85–1.8(m, 12H)Cyclo- hexyl, OH;1.9–2.2(m, 2H) CH₂;2.5(d, J=7H, 2H) CH₂;2.65–2.9(m, 2H)CH₂; 4.4–4.5(m, 1H)CHOH;5.35– 5.45(m, 1H)CHOCO;5.88 (dd, J=16Hz, 1H)CH=; 6.58(d, J=16Hz, 1H)CH=; 7.06(d, 1H)aromat. prot. 7.26(d, 1H) aromat. prot. | C₂₀H₂₄Cl₂O₃ 383.3 M.p.: 100–102° C. |
|  | o-CH₃ | H | CH₂ | aa | 0.2 | 93 | 0.85–1.8(m, 1H)Cyclohexyl OH; 1.95–2.2(m, 2H)CH₂; 2.29(s, 1H)CH₃;2.49(d, J=7Hz, 1H)CH₂;2.65–2.9 (m, 2H)CH₂;4.45–4.53(m 1H)CHOCO;5.7(dd, J= 16Hz, 1H)CH=;6.7(d, J=16Hz, 1H)CH=;6.95– 7.15(m, 3H)aromat. prot. | C₂₁H₂₈O₃ 328.45 M.p.: 99–101° C. |
| 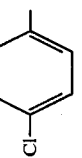 | o-Cl | H | CH₂ | ab | 0.25 | 94 | 1.8(broad s, 1H)OH; 1.75–2.1(m, 2H)CH₂;2.6– 2.85(m, 2H)CH₂;4.0(s, 2H)CH₂;4.35–4.45(m, 1H) CHOH;5.26–5.36(m, 1H) CHOCO;5.8(dd, J=16Hz, 1H)CH=;6.6(d, J=16Hz, 1H)CH=;6.95–7.35(m, 7H) aromat. prot. | C₂₀H₁₈Cl₂O₃ 377.25 |
|  | o-Cl | H | CH₂ | ac | 0.2 | 98 | 0.85–1.8(m, 12H)Cyclo- hexyl, OH;1.95–2.25(m, 2H)CH₂;2.55(d, J=7Hz, 1H)CH₂;2.6–2.9(m, 2H) CH₂;4.45–4.53(m, 1H) CHOCO;5.35–5.46(m, 1H) CHOCO;5.9(dd, J=16Hz, 1H)CH=;6.65(d, J=16Hz, 1H)CH=;7.05–7.3(m, 3H) aromat. prot. | C₂₀H₂₅Cl O₃ 348.86 |

TABLE 10-continued
| | o-CH₃ | H | CH₂ | ad | 0.15 | 72 | 1.5(broad s, 1H)OH; 1.75-2.1(m, 2H)CH₂;2.29 (s, 3H)CH₃;2.6-2.85(m, 2H)CH₂;3.98(s, 2H)CH₂; 4.32-4.4(m, 1H)CHOH; 5.21-5.31(m, 1H)CH=;5.6 (dd, J=16Hz, 1H)CH=;6.6 (d, J=16Hz, 1H)CH=;6.9- 7.15(m, 7H)aromat. prot. | C₂₁H₂₁O₃F 362.9 M.p.: 94-95° C. |
| 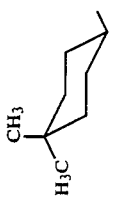 | o-Cl | p-Cl | CH₂ | ae | 0.24 | 69 | 0.85-1.8(m, 10H)CH₂,OH; 1.9-2.2(m, 2H)CH₂;0.9 (2s, 6H)CH₃;2.52(d, J= 7Hz, 2H)CH₂;2.64-2.86 (m, 2H)CH₂;4.41-4.52(m 1H)CHOH;5.33-5.44(m, 1H)CHOCO;5.87(dd, J= 16Hz, 1H)CH=;6.57(d, J=16Hz, 1H)CH=;7.06 (d, 1H);7.25(d, 1H) aromat. prot. | C₂₂H₂₈O₃Cl₂ 411.35 |
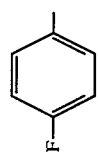
¹Cyclohexane/ethyl acetate = 1:1

Example 17

(+)-6S-[2-(2-(2-(4-Fluorophenyl)ethyl)phenyl)ethyl]-4R-hydroxy-3,4,5,6-tetrahydro-2H-pyran-2-one I'g Tab. 11

($R^1$=4-Fluorophenyl, $R^2$ and $R^3$=H, A-B=CH$_2$—CH$_2$, Z=CH$_2$—CH$_2$)

1 g of 10% Pd/C are prehydrogenated in 20 ml of absolute CH$_3$OH in a shaken vessel. Then 0.13 g (0.38 mmol) of compound Ig (Example 16), dissolved in 10 ml of absolute MeOH, is added. Hydrogenation is carried out at room temperature. After uptake of 10 ml of H$_2$ (109.), the hydrogenation is stopped, the catalyst is removed by filtration with suction, and the filtrate is concentrated in vacuo.

Yield: 0.12 g (93% of theory) of I'g (A-B=CH$_2$—CH$_2$).

$R_f$=0.12 (mobile phase: cyclohexane/ethyl acetate 1:1).

$^1$H NMR 270 MHz δ values in ppm: (cf. Tab. 11).

Examples 17a–17k

In a manner analogous to that described in Example 17 for compound I'g, it is possible to hydrogenate the compounds I (A-B=—CH=CH—) to give the compounds I' (A-B=CH$_2$CH$_2$) (Tabl. 11).

TABLE 11

$R^2, R^3$ = H
(A-B = —CH$_2$—CH$_2$—)

| $R^1$ | Z | Example 17 | $R_f^{(1)}$ E | Yield % | $^1$H NMR 270 MHz (CDCl$_3$) δ-values in ppm | Mass spectrum |
|---|---|---|---|---|---|---|
| cyclohexyl | —CH$_2$—CH$_2$— | a | 0.30 | 91 | 1.2–3.0(m,24H)CH,CH$_2$,OH; 4.38–4.46(m,1H)—C$\underline{H}$—CH; 4.7–4.8(m,1H)—C$\underline{H}$—OOO; 7.1(s,4H) aromat. protons | C$_{21}$H$_{30}$O$_3$ M = 330 M—H$_2$O = 312 |
| phenyl | CH$_2$—CH$_2$ | b | 0.28 | 49 | 1.7–2.1(m,5H)CH$_2$,CH; 2.6–3.0(m,8H)CH$_2$—CH$_2$,CH$_2$ 4.38–4.46(m,1H)—CH—CH; 4.7–4.85(m,1H)—CH—O—CO; 7.2–7.4(m,9H)aromat. protons | C$_{21}$H$_{24}$O$_3$ M = 324 |
| 4-Cl-phenyl | CH$_2$—CH$_2$ | c | 0.24 | 65 | 1.65–2.0(m,5H)CH$_2$,CH; 2.55–2.9(m,8H)—CH$_2$—CH$_2$, CH$_2$; 4.35–4.45(m,1H)—CH—OH; 4.65–4.78(m,1H)—CH—O—CO; 7.05–7.28(m,8H) aromat. protons | C$_{21}$H$_{23}$ClO$_3$ M = 358 |
| 3-CH$_3$O-phenyl | CH$_2$—CH$_2$ | d | 0.22 | 71 | 1.3(broad s,1H)CH; 1.7–2.0(m,4H)CH$_2$;2.6–3.0(m,8H)—CH$_2$—CH$_2$ OH$_2$;3.80(s,3H)OCH$_3$; 4.35–4.45(m,1H) CH—CH;4.65–4.8(m,1H)—CH—O—CO;6.7–6.85(m, 2H) aromat. prot.;7.15–7.3(m,6H) aromat. protons | C$_{22}$H$_{26}$O$_4$ M = 354 |
| 3-F$_3$C-phenyl | CH$_2$—CH$_2$ | e | 0.21 | 51 | 1.55(broad s,1H)CH;1.8–2.0(m,4H)CH$_2$ 2.6–2.95(m,4H)CH$_2$;2.95(s,4H)CH$_2$—CH$_2$; 4.35–4.45(m,1H)>CH—CH;4.65–4.78(m, 1H)>CH—OCO;7.1–7.2(m,4H) aromat. prot. 7.35–7.5(m,4H) aromat. protons | C$_{22}$H$_{23}$F$_3$O$_3$ M = 392 |
| 3,4,5-tri(CH$_3$O)-phenyl | CH$_2$—CH$_2$ | f | 0.35 | 72 | 3.78(s,6H)OCH$_3$;3.82(S,3H)OCH$_3$; | C$_{24}$H$_{30}$O$_6$ M = 414 |

TABLE 11-continued $$\text{(I}^1\text{)}$$

R², R³ = H
(A-B = —CH₂—CH₂—)

| R¹ | Z | Example 17 | $R_f^{(1)}$ E | Yield % | ¹H NMR 270 MHz (CDCl₃) δ-values in ppm | Mass spectrum |
|---|---|---|---|---|---|---|
| 4-F-phenyl | CH₂—CH₂ | g | 0.29 [α]$_D$ = 31.4 MeOH | 58 | 1.7–2.0(m,5H)CH₂,CH;2.6–2.95(m,8H)CH₂ CH₂,CH₂;4.37–4.45(m,1H)>CH—CH;4.65– 4.8(m,1H)>CH—OCO;6.9–7.2(m,8H)aromat. protons | C₂₁H₂₃FO₃ M = 342 |
| 2-CH₃-phenyl | CH₂—CH₂ | h | 0.27 | 62 | | C₁₂H₂₆O₃ M = 368 |
| 3-thienyl | CH₂—CH₂ | i | 0.23 | 49 | | C₁₉H₂₂O₃S M = 330 |
| cyclohexyl | CH₂ | j | 0.19³ | 97 | 0.9–1.3(m,5H)CH₂,CH;1.4–2.0(m,11H)CH₂, CH;2.5(d,I=8Hz,2H)CH₂;2.6–3.0(m,4H)CH₂; 4.35–4.45(m,1H) CHOH;4.65–4.8(m,1H) CHOCO;7.1–7.2(m,4H)aromat. protons | C₂₀H₂₈O₃ M = 3.16 |
| phenyl | CH₂ | k | 0.12¹ M.p. 114–115° C. | 95 | 1.6–1.9(m,5H)CH₂,OH;2.55–2.95(m,4H)CH₂; 4.05(s,2H)CH₂; 4.28–4.35(m,1H)CH—CH;4.55– 4.7(m,1H) CHOCO;7.1–7.3(m,8H)aromat. protons | C₂₀H₂₂O₃ M = 310 |
| 4-Cl-phenyl | CH₂ | l | 0.08¹ M.p. 99–101° C. | 93 | 1.6–1.9(m,4H)CH₂;1.8–2.05(broad s,1H) CH;2.6–2.95(m,4H)CH₂;4.0)s,2H)CH₂;4.3– 4.4(m,1H) CH—OH;4.55–4.8(m,1H)CHOCO;7.0– 7.3(m,8H) aromat. protons | C₂₀H₂₁ClO₃ M = 344 |
| 3-CH₃O-phenyl | CH₂ | m | 0.38² | 69 | 1.55–1.9(m,5H)CH,CH₂;2.55–2.95(m,4H)CH₂; 3.78(s,3H)OCH₃;4.02(s,2H)CH₂;4.3–4.4 (m,1H)CH—OH;4.55–4.8(m,1H) CHOCO;6.65– 6.8(m,2H) aromat. prot.; 7.1–7.3(m,6H) aromat. prot. | C₂₁H₂₄O₄ M = 340 |
| 3-F₃C-phenyl | CH₂ | n | 0.29 | 72 | | C₂₁H₂₁F₃O₃ M = 378 |

TABLE 11-continued (I¹)

[Structure: lactone ring with HO on one stereocenter, O on ring, ethylene linker to substituted phenyl with R¹-Z, R², R³ substituents]

R², R³ = H
(A-B = —CH₂—CH₂—)

R¹—Z—[phenyl with R², R³]

| R¹ | Z | Example 17 | $R_f^{(1)}$ E | Yield % | ¹H NMR 270 MHz (CDCl₃) δ-values in ppm | Mass spectrum |
|---|---|---|---|---|---|---|
| CH₃O, CH₃O, CH₃O- (3,4,5-trimethoxyphenyl) | CH₂ | o | 0.08¹ 0.25² | 87 |  | C₂₃H₂₈O₆ M = 400 |
| F-phenyl- | CH₂ | p | 0.12¹ | 62 | 1.6–1.9(m,5H)CH₂,CH;2.6–3.0(m,4H)CH₂; 4.0(s,2H)CH₂;4.3–4.4(m,1H)>CHOH;4.55– 4.8(m,1H)>CHOCO;6.9–7.2(m,8H) aromat. protons | C₂₀H₂₁FO₃ M = 328 |
| 3-methylphenyl (H₃C-) | CH₂ | q | 0.24³ M.p. 100–101° C. | 78 | 1.55–1.95(m,5H)CH₂,CH;2.30(s,3H)CH₃; 2.55–2.95(m,4H)CH₂;3.98(s,2H)CH₂;4.28– 4.35(m,1H)>CHOH;4.55(m,1H);6.9–7.2(m, 8H) aromat. protons | C₂₁H₂₄O₃ M = 324 |
| thien-2-yl (S) | CH₂ | r | 0.19 | 58 | 6.6–7.45(m,7H)aromat. prot. | C₁₈H₂₀O₃ M = 316 |

(1) Cyclohexane/EtOAc 1:1
(2) EtOAc
(3) n-Hexane/EtOAc 1:1
(4) Chloroform/EtOAc 9:1

Example 18

Preparation of the salts of the free dihydroxy acids of the compounds of the general formula Ia (+)-(E)-(3R,5S)-7[2-(2-(4-Fluorophenyl)ethyl)phenyl]-3,5-dihydroxy-6-heptenoic acid potassium salt (R¹ =

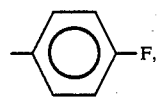
-F,

Z=CH₂—CH₂, R² and R³=H, R⁴=K⊕,
A-B=—CH=CH—)

0.1 g of compound Ig (Example 16) is dissolved in 5 ml of absolute EtOH. 2.9 ml of a 0.1 molar solution of KOH in EtOH are added to this solution at room temperature. After about 3 hours, the ester is no longer present on a thin-layer chromatogram (mobile phase cyclohexane/ethyl acetate 1:1). The ethanolic solution is concentrated in vacuo. The residue is Yield: 102 mg of white crystals of the K salt.
IR: C=O band 1610/1580 cm⁻¹.

It is possible in a manner analogous to that described in Example 18 to prepare the potassium salts of the relevant free dihydroxy acids of the compounds of the general formula Ia.

Example 19

Preparation of the methyl ester of the free dihydroxy acids of the general formula Ia Methyl (+)-(E)-(3R,5S)-7[2-(2-(4-fluorophenyl)ethyl)phenyl]-3,5-dihydroxy-6-heptenoate (R¹=

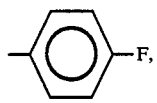

Z=—CH₂—CH₂, R² and R³=H, R⁴=CH₃, A-B=—CH=CH—)

0.4 g of compound Ig (Example 16) was dissolved in 10 ml of absolute MeOH. 1.3 ml of a 0.1 molar solution of NaOCH₃ in absolute MeOH was added to this solution at room temperature, and the mixture was stirred for about 1 hour. The solvent was then removed in vacuo, and the residue was taken up in water, the pH was adjusted to 7 at 0° C., and the solution was rapidly extracted with ethyl acetate, the extract was dried with MgSO₄, filtered, and the solvent was removed in vacuo. The title compound remained. Yield: 0.38 g of methyl ester $R_f$=0.18 (mobile phase: cyclohexane/ethyl acetate=1:1).

¹H NMR 60 MHz δ value in ppm.

3.65 (s, 3H)-OCH₃.

It is possible in a manner analogous to that described in Example 19 to prepare the methyl esters of the free dihydroxy acids of the general formula Ia. By replacement of methanol by other alcohols (R⁴—OH) it is also possible readily to prepare other corresponding esters Ia(R⁴=C₂H₅), i-C₃H₇, benzyl etc.).

We claim:

1. A 3-demethylmevalonic acid derivative of the formula I (δ-lactone)

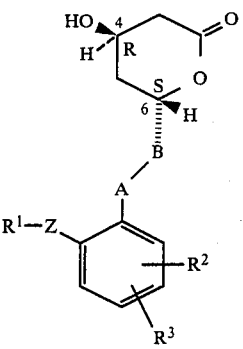

in which

A-B is a —CH=CH— group,

Z is a —CH₂— or —CH₂—CH₂— group,

R¹ is a cycloaliphatic hydrocarbon group which has 3 to 7 carbon atoms or a cycloaliphatic hydrocarbon having 3 to 7 carbon atoms which is substituted with 1 or 2 methyl groups, R² and R³ are halogen or alkyl having 1-4 carbon atoms.

2. A compound as claimed in claim 1, wherein, in formula I,

R¹ is cyclopentyl or cyclohexyl,

R² and R³ are halogen or alkyl having 1 to 4 carbon atoms.

3. A compound as claimed in claim 1, wherein, in formula I,

R¹ is cyclopentyl or cyclohexyl,

R² and R³ are hydrogen, 2-methyl, 2,4-dimethyl, 2-methyl-4-chloro, 2-chloro-4-methyl, 2-ethyl, 2-isopropyl, 2-isobutyl, 2-chloro, 2-fluoro-, 2-bromo, 2,4-dichloro, 2,4-difluoro.

4. A pharmaceutical composition for the prophylaxis and therapy of arteriosclerosis and hypocholesterolemia which comprises an effective amount of a compound as claimed in claim 1 or a pharmaceutically acceptable salt thereof together with a pharmaceutically acceptable carrier.

5. A method of using a compound as claimed in claim 1 for the prophylaxis and therapy of arteriosclerosis and hypercholesterolemia which comprises administering an effective amount of the compound of claim 1 to a host.

* * * * *